United States Patent [19]

Bair et al.

[11] Patent Number: 6,067,523
[45] Date of Patent: May 23, 2000

[54] SYSTEM AND METHOD FOR REPORTING BEHAVIORAL HEALTH CARE DATA

[75] Inventors: Steven L. Bair; Ronald L. Meredith, both of Birmingham, Ala.; Danny R. Tillotson, Altamonte Springs; Philip Inglis, Winter Park, both of Fla.

[73] Assignee: The Psychological Corporation, San Antonio, Tex.

[21] Appl. No.: 08/887,926

[22] Filed: Jul. 3, 1997

[51] Int. Cl.⁷ .................................................. G06F 17/60
[52] U.S. Cl. .................................................. 705/3; 705/2
[58] Field of Search ..................... 705/2, 3, 1; 128/897; 600/300

[56] References Cited

U.S. PATENT DOCUMENTS

| | | |
|---|---|---|
| 4,464,122 | 8/1984 | Fuller et al. . |
| 4,642,768 | 2/1987 | Roberts . |
| 4,648,037 | 3/1987 | Valentino . |
| 4,722,055 | 1/1988 | Roberts . |
| 4,750,121 | 6/1988 | Halley et al. . |
| 4,837,693 | 6/1989 | Schotz . |
| 4,839,804 | 6/1989 | Roberts et al. . |
| 4,933,842 | 6/1990 | Durbin et al. . |
| 4,969,094 | 11/1990 | Halley et al. . |
| 5,018,067 | 5/1991 | Mohlenbrock et al. ............... 600/300 |
| 5,084,819 | 1/1992 | Dewey et al. . |
| 5,136,502 | 8/1992 | Van Remortel et al. . |
| 5,207,580 | 5/1993 | Strecher . |
| 5,225,976 | 7/1993 | Tawil . |
| 5,262,943 | 11/1993 | Thibado et al. ..................... 600/300 |
| 5,301,105 | 4/1994 | Cummings, Jr. . |
| 5,327,341 | 7/1994 | Whalen et al. . |
| 5,359,509 | 10/1994 | Little et al. . |
| 5,377,258 | 12/1994 | Bro . |
| 5,423,324 | 6/1995 | Brill . |
| 5,435,324 | 7/1995 | Brill ..................................... 128/897 |
| 5,544,044 | 8/1996 | Leatherman . |
| 5,555,191 | 9/1996 | Hripcsak . |
| 5,560,005 | 9/1996 | Hoover et al. . |
| 5,583,758 | 12/1996 | Mellroy et al. ........................ 705/2 |
| 5,619,991 | 4/1997 | Slaone ................................. 600/300 |
| 5,692,501 | 12/1997 | Minturn . |
| 5,722,418 | 3/1998 | Bro ...................................... 1/1 |
| 5,724,575 | 3/1998 | Hoover et al. . |
| 5,835,897 | 11/1998 | Dang . |
| 5,879,163 | 3/1999 | Brown et al. . |

FOREIGN PATENT DOCUMENTS

| | | |
|---|---|---|
| 0 320 749 A2 | 6/1989 | European Pat. Off. . |
| 2252433 | 8/1992 | United Kingdom . |
| WO 91/06917 | 5/1991 | WIPO . |
| WO 95/32480 | 11/1995 | WIPO . |

OTHER PUBLICATIONS

Slack et al. Be Well! A Computer–Based Health Care Interview for Hospital Personnel. Copyright 1994, AMIA, Inc. pp. 12–16.

Wenner. Using Interview Software for Early Recognition of Behavioral Illness. Ambulatory Systems. Proceedings: Toward an Electronic Patient Record '96. pp. 301–307.

Behavioral Health Software Attract Attention by Mari Edlin, *Health Management Technology*, Dec. 1996. pp. 34–37.

*Primary Examiner*—Eric W. Stamber
*Assistant Examiner*—M. Irshadullah
*Attorney, Agent, or Firm*—Allen, Dyer, Doppelt, Milbrath & Gilchrist, P.A.

[57] ABSTRACT

The present invention relates to systems and methods for reporting behavioral health care data, and, more particularly, for creating displays and reports for aggregating data from patient treatment results. One feature permits the user to choose among patient progress indicators relative to a behavioral problem to be graphed versus time, along with one or more treatments, in order to gauge the effect of the treatment upon the behavioral problem. Another feature permits the generation of a narrative report that integrates fixed textual matter with data from the patient's electronic chart. An alternate embodiment of this feature also permits the composition of formats for a narrative report.

12 Claims, 37 Drawing Sheets

| Medications for Sample-Patient J Q | |
|---|---|
| Medication | |
| Prozac | |
| Tanormin | |
| Xanax | |
| Zoloft(Tablets) — 541 | |

Dosage: 25 Mg 1 TID
Quantity: 90
Refill: 3
Start: 01/05/1996
Expire: 01/05/1997
Route: Oral
Prescribe: Treatment for hypertension
Discontinue:

OK
Add.... — 543
Delete.... — 544

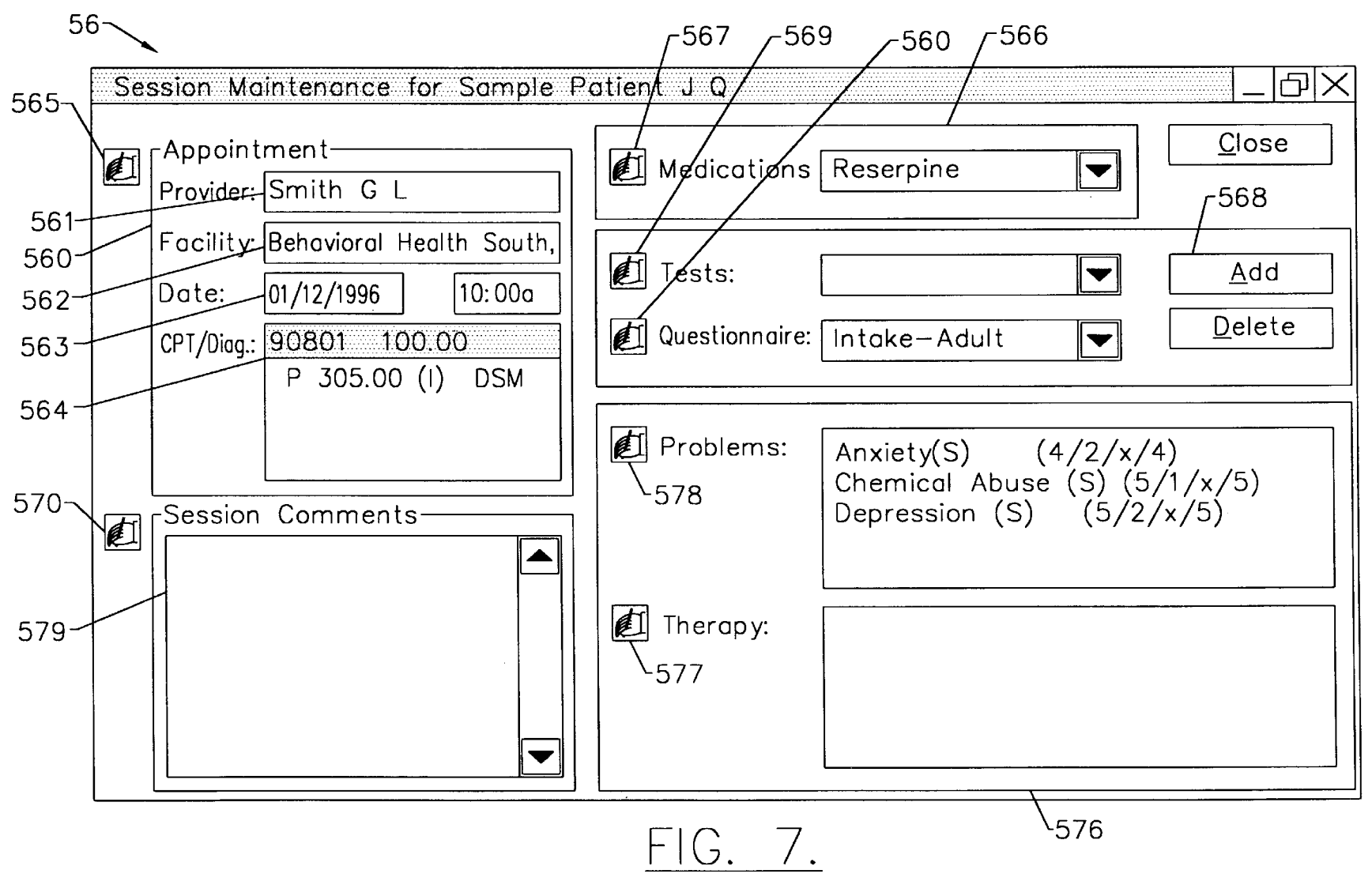

Session Maintenance for Sample Patient J Q

Appointment
- Provider: Smith G L
- Facility: Behavioral Health South,
- Date: 01/12/1996   10:00a
- CPT/Diag.: 90801  100.00
  P 305.00 (I) DSM Medications: Reserpine
Tests:
Questionnaire: Intake—Adult Problems:
Anxiety(S)      (4/2/x/4)
Chemical Abuse (S)  (5/1/x/5)
Depression (S)      (5/2/x/5)

Therapy:

Session Comments

Close
Add
Delete

FIG. 7.

Appointment for Sample Patient J Q

Provider: Smith G L
Facility: Behavioral Health South, P.C.

Appointment Date: 01/12/1996
Appointment Time: 10:00 ● AM ○ PM

OK
Cancel

CPT for Session:
90881 100.00 Initial Office Visit
P 305.00 Alcohol Abuse

Diagnoses in Treatment Plan
305.00 (P) DSM (I) Alcohol Abuse
296.22 DSM (I) Major Depressive Disorde
300.23 DSM (I) Social Phobia
301.4 DSM (II) Obsessive-Compulsive Pe
401.9 DSM (III) Hypertension, essentia
808.84 DSM (IV) Occupational problems
50.00 DSM (V) Serious symptoms OR impa Add from CPT Table....
Edit CPT Fee....
Remove CPT from Session Add from Diagnoses Table....
Edit Diagnosis Dates....
Delete Diagnosis....

Show All Diagnoses....

Post Charge/Payment....
Account Ledger....

FIG. 8.

Treatment Plans for Sample-Patient J Q

- Treatment Plan
  - Case Start 01/13/1996 thru 06/13/1997 Status: Active
  - Demographic Variables:
    - Income Level: $100,000+
    - Education Level: College
    - Number of Children: 3
  - Case Manager: Jones, Roger Trent
  - Case Comment: Patient has a history of problem drinking and sui
  - UR Schedule:
    - Every 5th 90844 Session
  - Provider: Smith, G L (Staff)
  - Diagnoses:
    - 305.00 DSM Axis I Alcohol Abuse
    - 296.22 DSM Axis I Major Depressive Disorder, Single Epis
    - 300.23 DSM Axis I Social Phobia
    - 301.4 DSM Axis II Obsessive-Compulsive Personality Diso
    - 401.9 DSM Axis III Hypertension, essential
    - 000.04 DSM Axis IV Occupational problems
    - 50.00 DSM Axis V Serious symptoms OR impairment in fur
  - CPT/Sessions:
    - 90801 Sessions: 01 Used: Initial Office Visit
    - 90844 Sessions: 15 Used: Office Visit 50 Minutes
    - 90862 Sessions: 03 Used: Pharmacologic management
  - Level of Care:
    - Routine OP Buttons: History..., Request..., HCFA Info..., Close, Add..., Edit, Delete Managed Care
- Case Sessions
  - Approved: 19
  - Used: 14
- Total Sessions
  - Approved: 19
  - Used: 14

FIG. 9.

| Description | Questionnaire |
|---|---|
| Aggressiveness Potential | 90 |
| Anxiety Disorders Evaluation | 40 |
| Child/Adolescent Rx. | 67 |
| Consultation Note/Request | 58 |
| Disability Evaluation – Adult | 75 |
| Disability Evaluation – Child | 73 |
| Disability Evaluation – Teen | 74 |
| Family Therapy | 65 |
| Group Individual Note | 62 |
| Group Therapy | 61 |
| HAI-EAP Adolescent | 621 |

FIG. 18.

Master Question Table

Search:

| Question Description | Number |
|---|---|
| AA Involvement | 61 |
| AA/NA Participation | 5381 |
| Ability to Make Work Decisions | 617 |
| Ability to Manage Funds | 618 |
| Abstraction Ability—MSE | 552 |
| Academic Goals | 502 |
| Academic Performance—Adolescence | 886 |
| Academic Performance—Adult | 885 |
| Academic Performance—Childhood | 435 |
| Academic Potential | 436 |
| Accept Individuality—Family | 5340 |
| Acceptance of Individuality | 733 |
| Acceptance of Others | 350 |
| Acceptance of Others | 366 |
| Accessibility to Feelings | 343 |
| Accomplishment of Goals | 675 |
| Active Involvement | 360 |

Question Sequence
- Question Description
- Question Number

Question Options: Single Entry

Question Type: Answer/Comment

Genus Office: TPC00001

Present/Extended Questionnaire Sentence: The client's involvement with AA is:

Copyright:

[Buttons: Close, Add..., Save, Delete, Questionnaires, Answers..., Clone..., Copyright]

FIG. 20.

Select Question

Search: [ ]

| Description | Question |
|---|---|
| AA Involvement | 61 |
| AA/NA Participation | 5381 |
| Ability to Make Work Decisions | 617 |
| Ability to Manage Funds | 618 |
| Abstraction Ability – MSE | 552 |
| Academic Goals | 502 |
| Academic Performance – Adolescence | 886 |
| Academic Performance – Adult | 885 |
| Academic Performance – Childhood | 435 |
| Academic Potential | 436 |
| Accept Individuality – Family | 5340 |
| Acceptance of Individuality | 733 |
| Acceptance of Others | 350 |

[Select] [Cancel]

FIG. 21.

Add New Question

Description:

Protect/Guided Questionnaire Sentence

Question Type
- Answer/Comment
- Comment Only
- Result
- Questionnaire Terminator
- Procedure Terminator

Entry Option
- Single Answer Only
- Multiple Answers

Likert Scaleable
- Yes
- No

Copyright Holder

▶ Year:

[Close] [Add...] [Save] [Cancel]

Questionnaire Narrative Format

| Questionnaire | | Narrative Format | |
|---|---|---|---|
| Aggressiveness Potential | (000090) | Aggressiveness Potential | (AP) |
| Disability Evaluation - Adult | (000075) | Adult Disability - History | (AP-1) |
| Improvement Index | (000098) | Improvement Index | (II) |
| Lethality Profile | (000089) | Lethality Profile | (LP) |
| Managed Care - Brief Med Eval | (000103) | Managed Care - Brief Med Eval 1 | (MC-HME-1) |
| Managed Care - Brief Review | (000079) | Managed Care - Brief Review | (ECBR) |
| Managed Care - Client Report | (000108) | Managed Care - Client Report | (MC-CR) |
| Managed Care - Med Intake | (000102) | Managed Care - Med Intake 1 | (MC-MED1) |
| Managed Care - Med Review | (000105) | Managed Care - Med Review 1 | (MC-MEDR1) |
| Managed Care - Satisfaction | (000107) | Satisfaction Survey | (SATISFY) |
| Managed Care Quality Concerns | (000097) | Managed Care Quality Concerns | (MCIC) |
| MMPI Report | (000087) | MMPI - History | (MEPI-1) |
| Outcome Measures | (000084) | Treatment Outcome Report | (OUTCOME) |
| Psychological - Adult | (000002) | Adult Psychological - History | (AP-1) |
| Psychological - Child | (000000) | Child Psychological - History | (CP-1) |
| Psychological - Data Report | (000016) | Psychological - Data Report | (P DMUE) |

OK

Narrative Note Formats

Search: _____

| Formal ID | Formal Description |
|---|---|
| AD-5 | Adult Disability – Cognitive |
| AD-7 | Adult Disability – Conclusions |
| AD-8 | Adult Disability – Data |
| AD-1 | Adult Disability – History |
| AD-3 | Adult Disability – MSE |
| AD-6 | Adult Disability – Personality |
| AD-4 | Adult Disability – Prim Domain |
| AD-2 | Adult Disability – Work/Med |
| AI-4 | Adult Intake – Adjustment |
| AI-2 | Adult Intake – Development |
| AI-3 | Adult Intake – Family/Educ. |
| AI-1 | Adult Intake – History |
| AP-3 | Adult Psychological – Beh Obs |
| AP-6 | Adult Psychological – Cognitiv |
| AP-7 | Adult Psychological – Conclude |

Format Sequence
○ Format ID
● Format Description

[Close] [Add...] [Edit...] [Delete] [Rename...] [View] [Clone]

FIG. 24.

Behavioral Health South, P.C.

Narrative: MC-SR — Managed Care — Session Review

------------------------Permanent Blank Line--------------------------
Center Line—><UnderlineOn><BoldOn>MANAGED CARE SESSION REVIEW<BoldOff><UnerlineOff>
------------------------Permanent Blank Line--------------------------
------------------------Permanent Blank Line--------------------------
Name......................<@Name (First I. Last)—Patient@>
SS Number..............<@Social Security Number—Patient@>
Date of Birth...........<@Date of Birth—Patient@>
Date of Evaluation...<@Chart Note Date—Misc@>
Age..........................<@Age—Patient@>
Sex...........................<@Sex (male/female)—Patient@>
Marital Status..........<@Marital Status—Patient@>
Chart Number..........<@Chart #—Patient@>
Chart Entered By....<@Chart Entered By—Misc@>
Diagnoses................<@Diagnostic Code I (Header)—Patient@>
                              <@Diagnostic Code II (Header)—Patient@>
                              <@Diagnostic Code III (Header)—Patient@>
                              <@Diagnostic Code IV (Header)—Patient@>
                              <@Diagnostic Code V (Header)—Patient@>
------------------------Permanent Blank Line--------------------------
------------------------------Section 001------------------------------
Assessment was based on <@Assessment@>.

The general treatment approaches utilized during this session included <@Intervention@>.

Specific techniques included <@Techniques@>.

A consultation was completed on <@Mr. or Mrs.—Misc@> <@Name (Last)—Patient@> regarding <@Consultation Focus@> by <@his/her—Misc@> <@Consultee@>.
------------------------------Section 002------------------------------
<@Mr. or Mrs.—Misc@> <@Name (Last possessive)—Patient@> attitude was <@Attitude — Client@>.

The content of the session was focused on <@Content — Session@>

Subjective distress was assessed as <@Subjective Distress@>.

<@Personality Organization@>.

<@Mr. or Mrs.—Misc@> <@Name (Last)—Patient@> is experiencing <@Cognitive Impairment@> in cognitive functioning.

<@He/She—Misc@> demonstrated <@Interpersonal Impairment@> in interpersonal relationships, <@Emotional Impairment@>, and Managed Care — Session Review (MC-SR)    Page 1

FIG. 26A.

<u>Behavioral Health South, P.C.</u>

Narrative: MC-SR – Managed Care – Session Review
___

<@Level of Job Impairment@>.
<@He/She-Misc@> <@Global Psych Adjustment@>.
--------------------------------Section 003--------------------------------
<@Mr. or Mrs.-Misc@> <@Name (Last)-Patient@> <@Responsiveness to Therapy@>

<@Global Improvement@>.

<@He/She-Misc@> <@Prognosis/Continued Treatment@>.

Issues to be addressed during the next session include <@Session Prompt@>.

<@Mr. or Mrs.-Misc@> <@Name (Last)-Patient@> <@Return Appointment – Singular@>
--------------------------------Section 004--------------------------------
<@Chart Note Comment-Misc@>
--------------------------------Section 005--------------------------------
<@BEHAVIORS/GOAL/LAST5@>
--------------------------------Section 006--------------------------------
----------------------------Permanent Blank Line----------------------------
----------------------------Permanent Blank Line----------------------------
----------------------------Permanent Blank Line----------------------------
----------------------------Permanent Blank Line----------------------------
<@Signature Line Misc@>
<@Name (First I. Last, Suffix)-Provider@>
<@Professional Title-Provider@>

Managed Care – Session Review (MC-SR)     Page 2

FIG. 26B.

Behavioral Health South, P.C.

MANAGED CARE SESSION REVIEW

| | |
|---|---|
| Name | John Q. Sample-Patient |
| SS Number | 111-11-1111 |
| Date of Birth | September 4, 1950 |
| Date of Evaluation | February 3, 1996   10:00a |
| Age | 45 |
| Sex | male |
| Marital Status | married |
| Chart Number | 000001 |
| Chart Entered By | Administrator, |
| Diagnoses | Axis I 296.22 Major Depressive Disorder, Single Episode, Moderate   (DSM) |
| | Axis I 300.23 Social Phobia   (DSM) |
| | Axis I 305.00 Alcohol Abuse   (DSM) |
| | Axis II 301.4 Obsessive-Compulsive Personality Disorder   (DSM) |
| | Axis III 401.9 Hypertension, essential (DSM) |
| | Axis IV 000.04 Occupational problems (DSM) |
| | Axis V 50.00 Serious symptoms OR impairment in functioning   (DSM) |

Assessment was based on an in-session observation. The general treatment approaches utilized during this session included brief psychodynamic therapy.

271 — Dr. Sample-Patient's attitude was overly solicitous, provocative and resistive. The content of the session was focused on fears/insecurities, grief/loss, noncompliant behavior and social concerns. Subjective distress was assessed as moderate. Personality structure was intact and functional. Dr. Sample-Patient is experiencing mild impairment in cognitive functioning. He demonstrated mild impairment in interpersonal relationships, minimal emotional impairment, and mild impairment in job performance. He presents as generally well adjusted.

Dr. Sample-Patient is interested and responsive to therapy. Overall level of improvement was major. He will likely benefit from continued treatment. Issues to be addressed during the next session include follow-up with the family and review of the marital situation. Dr. Sample-Patient was scheduled to return in two weeks.

Target Behaviors

| Problem | Goal | Rating | Session |
|---|---|---|---|

Sample-Patient J Q                                                                 Page 1

FIG. 27A.

<u>Behavioral Health South, P.C.</u>

| | | | |
|---|---|---|---|
| Anxiety (S) | 2 | 3 | 02/03/1996 |
| | | 4 | 01/31/1996 |
| | | 5 | 01/26/1996 |
| | | 4 | 01/19/1996 |
| | | 4 | 01/12/1996 |
| Depression (S) | 2 | 3 | 02/03/1996 |
| | | 5 | 01/31/1996 |
| | | 4 | 01/26/1996 |
| | | 5 | 01/19/1996 |
| | | 5 | 01/12/1996 |
| Chemical Abuse (S) | 1 | 4 | 02/03/1996 |
| | | 5 | 01/31/1996 |
| | | 5 | 01/26/1996 |
| | | 5 | 01/19/1996 |
| | | 5 | 01/12/1996 |

--- not on file
not on file

Add New Followup Questionnaire Group

Title:

Questionnaire:

Send Questionnaire to
- ● Patients
- ○ Providers of Record
- ○ Providers of Session
- ○ Referrals Sample Size
- ● All
- ○ Maximum number of recipients Size:

Time Frame
- ● No specified period
- ○ Specific period

From: / /   To: / /

Close
Add
Save
Cancel

SYSTEM AND METHOD FOR REPORTING BEHAVIORAL HEALTH CARE DATA

BACKGROUND OF THE INVENTION

1. Field of the Invention

The present invention relates to systems and methods for reporting behavioral health care data, and, more particularly, for creating displays and reports for aggregating data from patient treatment results.

2. Description of Related Art

Health information systems in general, and behavioral health information systems in particular, have been the subject of considerable development efforts. Increasing demands have been placed by regulatory agencies and "hosts," which comprise the insurance companies, health-maintenance organizations, or hospitals that typically approve and pay for a care regimen for a patient. Extensive record-keeping is required, as well as extensive forms generation, time-intensive but non-revenue-generating activities.

Behavioral health care systems share some characteristics with other types of health care systems, including the need for data handling and transfer and billing functions. However, the results achieved with knowledge gleaned from the behavioral sciences until recently have been resistant to quantification and have endured the label of being "soft." For example, it is relatively simple to deduce that a patient can in most cases be cured of a particular type of infection with a dosage of an antibiotic administered over a period of time. However, similar deductions are more difficult to achieve with a behavioral health problem: How many sessions will it take to "cure" a depressed person? What does "cure" actually mean? Therefore, it would be desirable to be able to rate a severity of a behavioral health problem and to track the patient's improvement over time, including all the variables that comprise the treatment (type and duration of therapy, medication).

In a currently typical provider environment, such as a clinic, several therapists may treat patients on an outpatient basis. On a first visit the patient spends time filling out an information sheet, including demographic (i.e., social security number, name, and address) and insurance information. This handwritten information is then transcribed by a clinic employee and entered into a locally maintained database. Following a patient session, a form is generated, either manually or via the computer, and mailed or faxed to the host. The form contains one or more billing codes, such as those contained in the *CPT Code Table*, a widely used standard.

At the host site, the data on the form are correlated with a host database to ensure that the patient has a current policy and that the service provided is covered by that policy. This is usually undertaken by a case manager or claims adjudicator, who then either approves or disapproves the service for payment to the provider.

In the behavioral health field, a therapist typically diagnoses a patient's behavior(s) (e.g., absenteeism, acting out) and problem(s) (e.g., anxiety, depression) using the criteria set forth in the *Diagnostic and Statistical Manual of Mental Disorders* (DSM) and makes detailed handwritten chart notes expanding upon the patient's status. The DSM codes are relayed to the host, accompanied by the CPT code(s), with a request for payment and/or request for treatment approval.

Should the service recommended or provided fall outside the bounds of the patient's coverage, for example, if the patient has not improved sufficiently after a prescribed series of sessions, the provider will have to request additional sessions. Such a request may occur, for example, by sending case notes to the host, which again will have to be reviewed by a case manager.

Another area in which information systems have been applied is in treatment outcome evaluation, wherein a test or a series of tests is repeated at specified time intervals in order to monitor a patient's progress during therapy.

Yet another area of usefulness for information systems is in the establishment of a sufficiently large database to enable the calculation of average treatment outcomes. Such an evaluation is intended to provide an indication of treatment norms for a range of behavioral problems and severities. This will enable a host and/or provider to assess the relative effectiveness of a particular patient's treatment over time as compared with the norm. Such data would also be effective in aggregating results for a particular provider site (e.g., clinic) or therapist.

A health resource consumption system has been described by Mohlenbrock et al. (U.S. Pat. No. 5,018,067); an apparatus for measuring psychotherapy outcomes, by Brill (U.S. Pat. No. 5,435,324; and a microcomputer-based mental health information system, by McCullough et al. (*American Psychologist* 41, 207–14, 1986).

There is no known system that integrates and automates all the behavioral health care provider functions, including maintaining patient records, monitoring patient progress, performing scheduling operations, preparing billing and clinical reports, sending and receiving patient information directly online with a host system, and interfacing with an external database for amassing behavioral health care statistics. Further, there is no known interrelated host system that links multiple provider sites for managing clinical and financial data and permits automated case management, data aggregation, a treatment plan formulary, a query tool, and executive reporting capabilities.

SUMMARY OF THE INVENTION

It is therefore an object of the present invention to provide a behavioral health care optimization system and method for integrating patient chart, previous treatment, and treatment plan information, thereby minimizing requirements for human interaction.

It is another object to provide such a system that is compatible with both a host and a provider architecture.

It is an additional object to provide such a system and method for automating approval for treatment by the host site.

It is a further object to provide such a system and method that can electronically communicate selected information to a data-collection center for amassing a database of behavioral treatment outcome data.

It is yet a further object to provide such a system and method for displaying treatment goals with medications and interventions.

It is yet another object to provide such a system and method that permit the creation of customized questionnaires and the cross-referencing of a particular common question's results.

It is yet an additional object to provide such a system and method that permit user-defined branching within a questionnaire.

These objects and others are attained by the present invention, a system and method for reporting behavioral health care data. The system preferably comprises two interrelated systems, one resident within a computer housed at the provider site, which typically includes an office of a behavioral health care worker, such as a psychiatrist, psychologist, or social worker. The provider site may also be a hospital or clinic having a plurality of therapists liked via, for example, a local-area network. The second linked system is resident in a computer at the host site, which is typically a central office of an insurance company, health maintenance organization, or managed care organization. The host site may also be a hospital.

The provider system comprises means for performing a plurality of in-house functions, including assisting providers in electronically performing and recording clinical functions. The provider system also comprises means for displaying and entering results for one or more tests chosen from a group of empirically validated assessments and custom questionnaires. The provider system further comprises means for displaying outcome data versus time in graphical form, superimposed with medication and intervention data, and for monitoring patient progress, tracking a selected outcome measure.

Another important feature of the provider system is a means for electronically communicating with the host site computer, which permits electronically managing clinical and financial data, substantially without human intervention. Means are resident within the provider and host systems for achieving data transfer, including requests and approvals for treatment and payment, automatically, so long as the requests fall within a predetermined set of parameters resident within the host computer. Such parameters may also have been downloaded into the provider computer. Should a request not fall within this set of parameters, means are also provided for referring the request to a case manager and for transmitting the case manager's determination back to the provider system. The set of parameters for treatment typically comprise a set of rules that may be different for each plan, the rules governing, for example, how many treatment sessions are automatically granted for a particular behavioral problem reported by the patient. These rules are set at the host site and are fixed unless the host management makes a determination that a rule needs to be changed. Such a determination may be based, for example, on the results of statistics gathered from a plurality of provider sites or a change in a plan governing a particular set of patients.

The host system also includes means for tracking treatment plans and maintaining patient records. The host system also includes a database of provider profiles for use in recommending a therapist to a client based on selected criteria such as geographical location and area(s) of specialization.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF THE DRAWINGS

FIG. 5 illustrates an exemplary medications screen.

Figure 6:
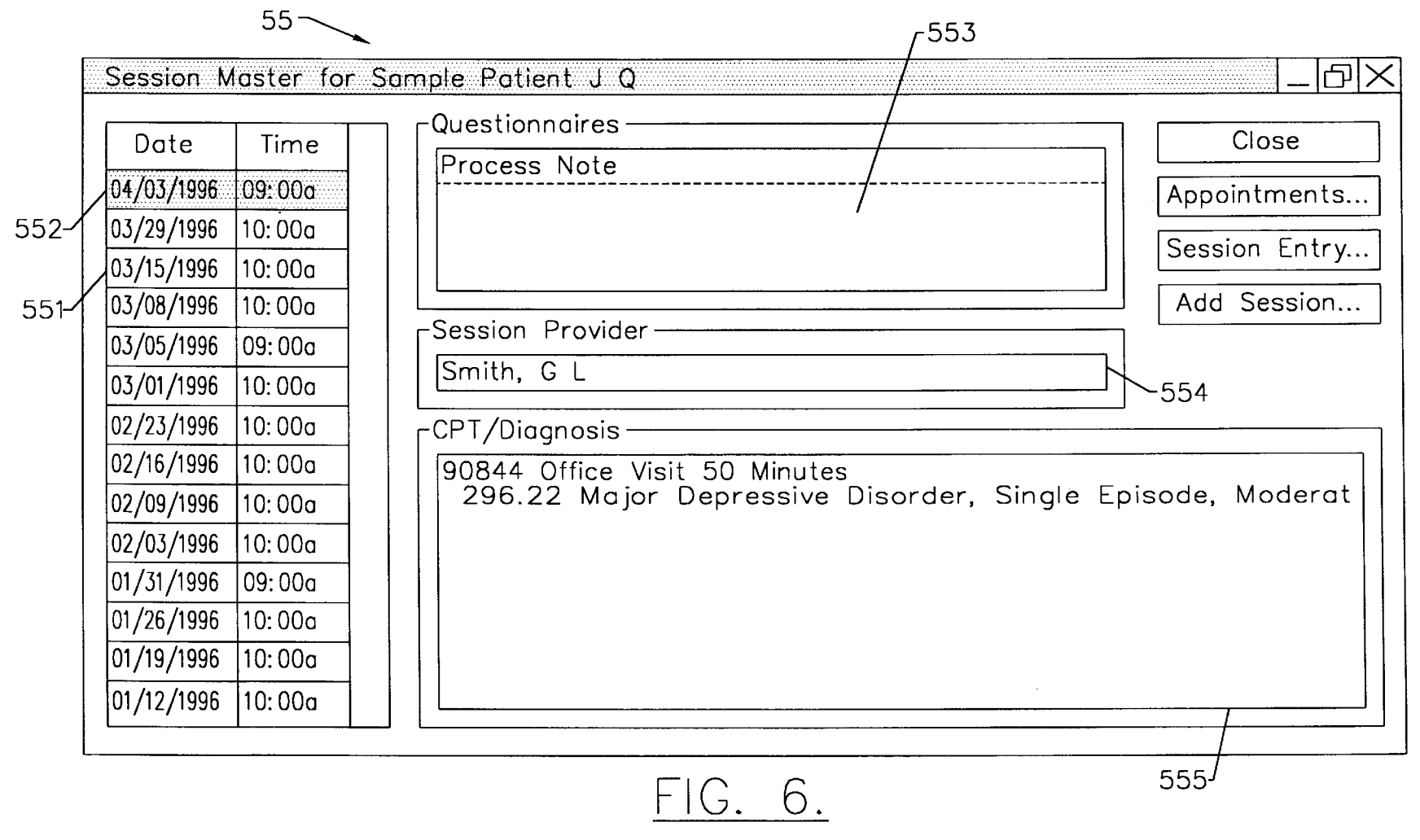

FIG. 6 illustrates an exemplary session master screen.

FIG. 7 illustrates an exemplary session maintenance screen.

FIG. 8 illustrates an exemplary appointment information screen.

FIG. 9 illustrates an exemplary treatment plan screen.

FIG. 18 illustrates an exemplary select questionnaire screen.

FIG. 20 illustrates an exemplary master question table screen.

FIG. 21 illustrates an exemplary select questions screen.

FIG. 22 illustrates an exemplary add new question screen.

FIG. 23A illustrates an exemplary questionnaire/narrative linkage screen.

FIG. 24 illustrates an exemplary screen for choosing a narrative note format.

FIG. 26 illustrates an exemplary narrative format structure, with FIG. 26A containing the first page and FIG. 26B, the second page of the format.

FIG. 27 illustrates a narrative report created from the narrative format structure of FIG. 26A,B, with FIG. 27A containing the first page and FIG. 27B, the second page of the report.

FIG. 32 illustrates an exemplary screen for creating a followup questionnaire group.

DETAILED DESCRIPTION OF THE PREFERRED EMBODIMENTS

A description of the preferred embodiments of the present invention will now be presented with reference to FIGS. 1–34.

Host-provider Systems and Interactions

Figure 1:
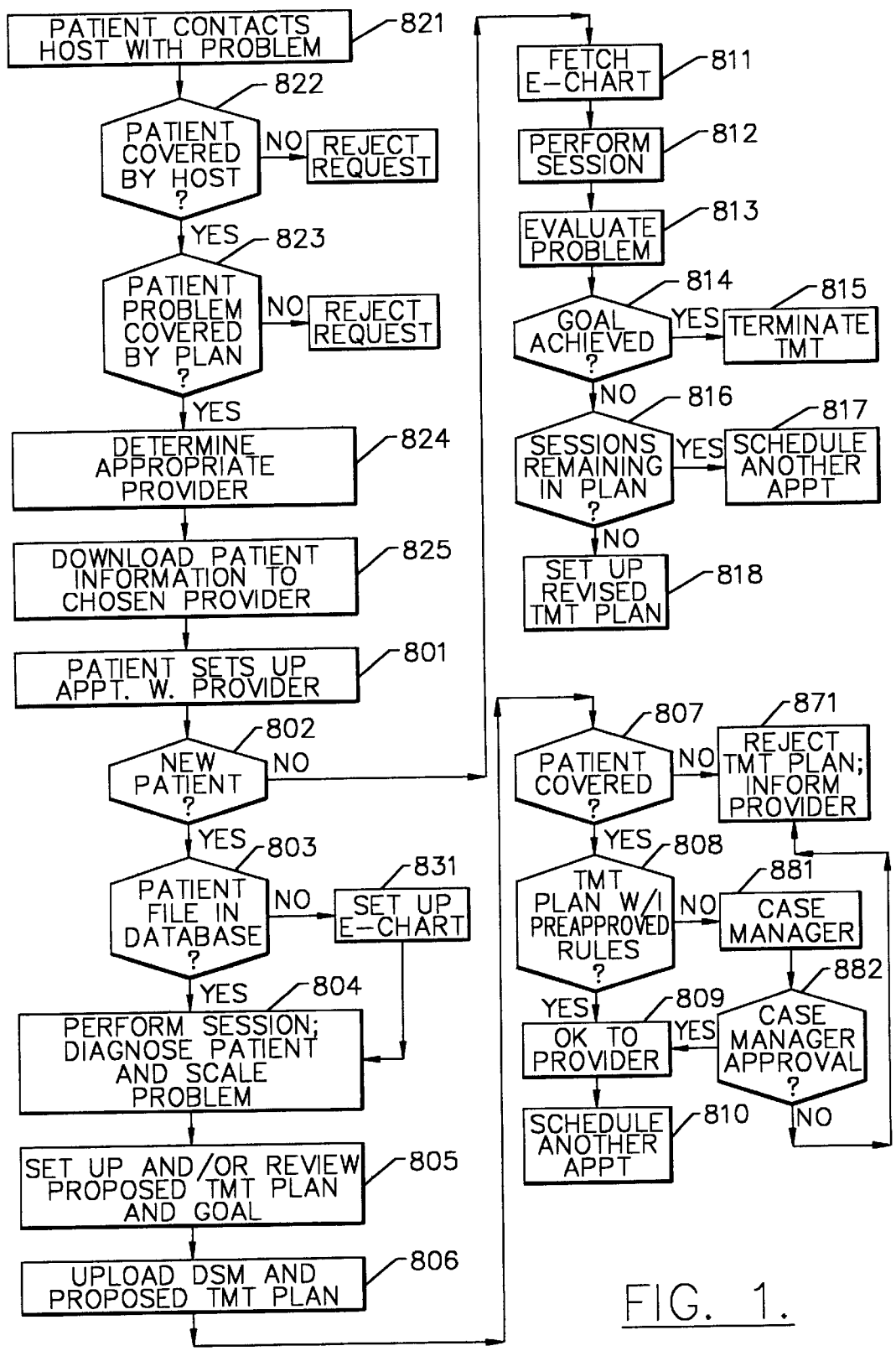
FIG. 1 is a flowchart of exemplary host-provider interactions.

A logic flowchart of an exemplary host-provider interaction comprising obtaining host site approval for and carrying out a treatment plan for a patient is given in FIG. 1. Reference is also made to elements in FIG. 2, which illustrates an exemplary hardware and software configuration for the host-provider system 10.

At step 801 a patient sets up an appointment at a provider site. Such an appointment can be initiated by the host or the patient. A determination is made at step 802 as to whether he/she is a new patient by checking against a patient list housed in a database 321 in the provider computer 32. If the patient is new, a check is made at step 803 as to whether this patient's electronic chart has already been downloaded from the host computer 200.

It is an important feature of the present invention that a patient's demographic and treatment information can be downloaded automatically from a host site without being requested. This occurs by a patient's requesting treatment directly from the host at step 821. The host first checks at step 822 that the patient has a policy, and whether the problem reported by the patient is covered by his policy at step 823. The host site then checks against its provider database at step 824 to recommend a provider to the patient based upon criteria such as geographical location and provider area(s) of specialization. Then, during a subsequent connect time between that provider and the host, the patient's pertinent information is downloaded directly into the provider's database at step 825, where it will be available for access by the provider at step 803, along with a preapproved treatment plan (for example, 5 therapy sessions of 1-hour duration plus a course of medication for depression).

If the new patient's information has not yet been entered, an electronic chart is set up at step 831 with information provided by the patient.

Typically the patient is then assigned to a therapist at step 804, who makes an initial behavioral diagnosis during a session using a table housed in the computer database that comprises the DSM codes. The therapist also rates the severity of the problem and enters a goal rating and a therapy treatment (tmt) plan aimed at achieving that goal into the patient's electronic chart at step 805. Alternatively, a treatment plan may have been included with downloaded patient information at step 825, in which case it will already be resident in the patient's electronic file.

During the next connect with the host, the DSM codes and proposed treatment plan are uploaded to the host at step 806, if the patient has indicated that he/she is insured by that host, and if that host is using the system of the present invention. At the host site, an automatic check is made at step 807 that the patient is covered. If not, the treatment plan is rejected at step 871, and the provider is so notified during the next download. If the patient is covered, a check is next made that the proposed treatment plan falls within the applicable set of treatment approval rules at step 808. If not, the file is referred for human intervention to a case manager at step 881, who decides whether to approve the treatment plan at step 882. If approval is not granted, the treatment plan is rejected and the provider is notified (step 871). If approval is granted, or if the treatment plan fell within the preapproved rules, the host so informs the provider electronically during a download at step 809. Then an appointment can be scheduled for the patient with the provider at step 810.

An approval from the host site may also contain instructions to administer one or more instruments to the patient, which should then be incorporated into the treatment plan. Such instruments, which may include tests and/or questionnaires, can also be mandated by the host to be administered at given intervals in order to gauge patient progress.

Returning to step 802, treatment for a returning patient proceeds by calling up the patient's electronic chart at step 811 and proceeding with the scheduled session at step 812. By the end of the session, the therapist should be able to make a determination at step 813, whether by testing or asking a series of questions from a questionnaire, as to the patient's progress. By referring to the electronic chart, the therapist can see at step 814 whether the patient has achieved the rating chosen as a goal for the problem being treated. If the goal has been achieved, treatment can be terminated at step 815.

If the goal has not yet been achieved, the therapist is able to check at step 816 whether there are further sessions remaining on the approved treatment plan. If there are, another appointment should be scheduled at step 817. If there are not, the therapist will typically set up a revised treatment plan at step 818 and request approval for the new plan by returning to step 806. This revised treatment plan request then is evaluated electronically as outlined above, only needing human intervention if the predetermined set of rules does not permit an approval of the request. In the depression example given above, the set of rules may include automatic approval for an additional five sessions of therapy if the patient has not improved to the goal rating.

It can be seen that the host-provider system 10 of the present invention significantly reduces the need for human intervention in a large proportion of situations for which a rule-based logic can be applied, only requesting the attention of a case manager under conditions that fall outside the coverage boundaries. The system contains virtually unlimited flexibility, since the rules and databases can be updated as desired.

Hardware Systems

Figure 2:
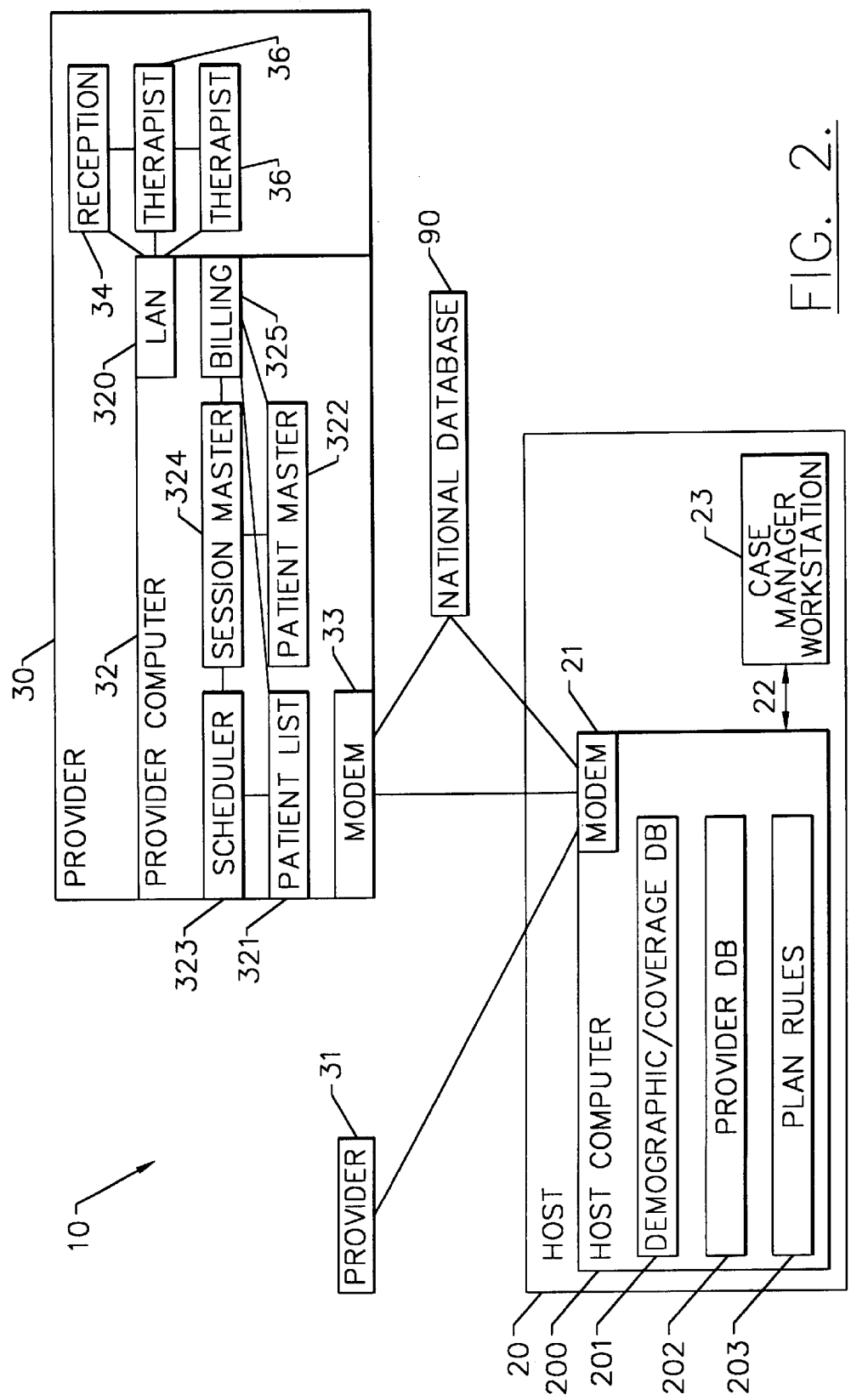
FIG. 2 is a schematic diagram of a host-provider system configuration and the structure of a host site and a provider site.
Figure 3:
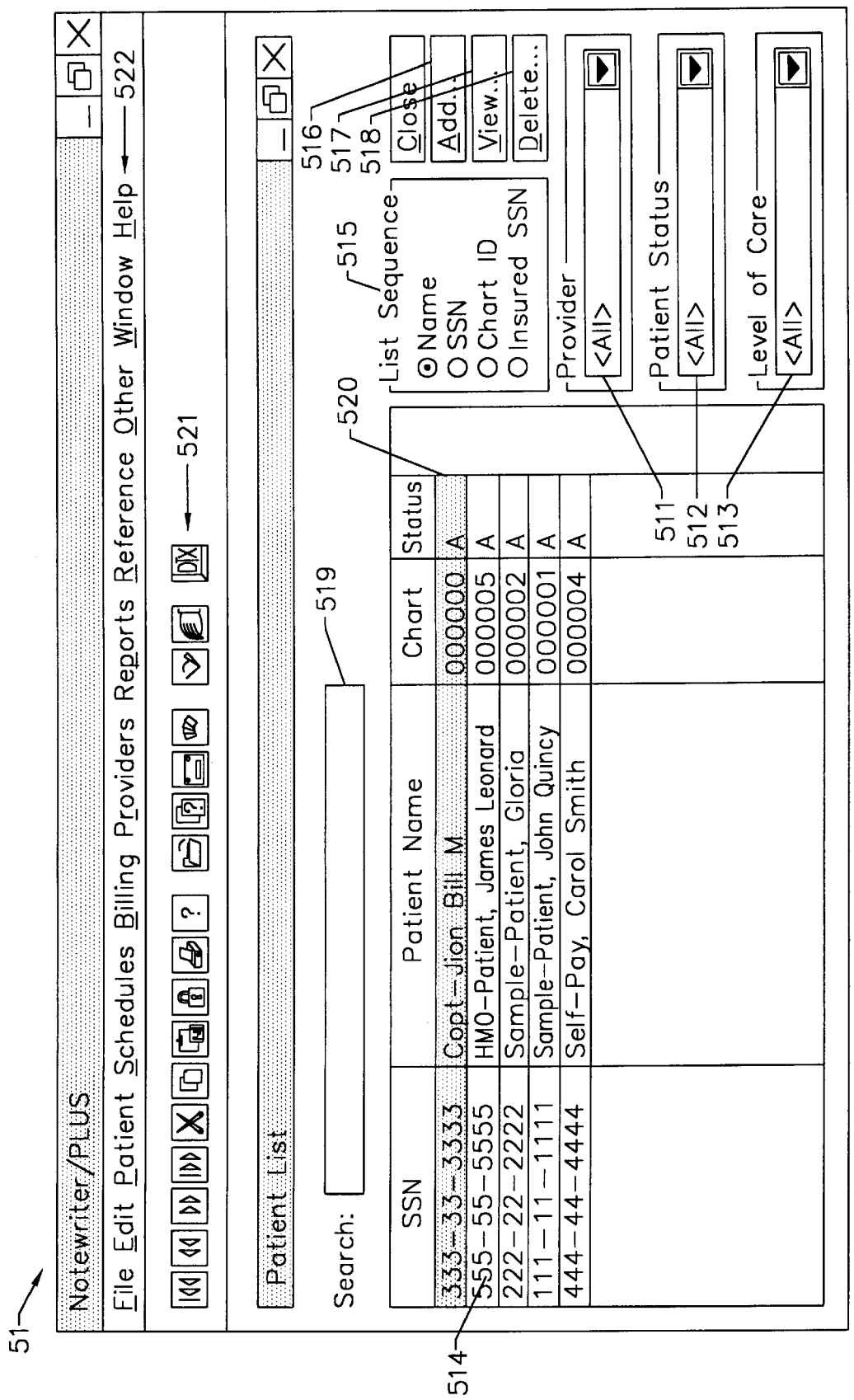
FIG. 3 illustrates an exemplary patient list screen.
Figure 4:
FIG. 4 illustrates an exemplary patient master screen.

A schematic diagram of a hardware and software configuration for a host-provider system 10 of the present invention is presented in FIG. 2. Two exemplary configurations are incorporated: In one configuration a host site 20 is in direct communication with a provider site 30, a situation that would obtain for a private practitioner in communication with an insurance company, for example. In another configuration the host site 20 is in communication with a local area network (LAN) system 320, which in turn is in communication with a plurality of provider sites. This situation would be found, for example, at a clinic having a plurality of therapists 36 and a central receptionist/administrator 34. Of course, it is to be understood by one of ordinary skill in the art that each provider will likely be in communication with a plurality of host sites; that is, each provider could be approved for coverage by different insurance companies, health maintenance organizations, etc. Communication then would be initiated between a provider and that host site by whose plan a particular patient is covered. The system provides sufficient flexibility that different sets of information can be mandated and sent to different host sites, with each having its own protocol.

In either of the configurations shown, each provider system at the provider site, as illustrated for provider site 30, comprises at least one provider computer 32, such as a 486-DX100 (32 MB RAM, 500 MB free hard disk, and a 14.4 bps modem 33), that may be networked via LAN 320 (10 Mb/100 Mb CAT 5 certified cable plant, Novell 3.1 or 4.1x, Windows/NT® 3.1 or higher) at the provider site 30, for example, to a reception workstation 34 and at least one, but typically a plurality of, therapist workstations 36 (486-DX100 or higher, 16 MB RAM, 100 MB free disk space SVGA display, 800×600, pointing device). Reception terminal 34 may be used for performing functions such as appointment scheduling, billing, and entering demographic information and updates.

The host site 20 preferably comprises a LAN server computer 200 (486-DX100, 64 Mb RAM, 1.2 Gb HDD per 15 concurrent users) and a modem 21 (14.4 bps v. 34), with one port per 10 provider sites. The LAN specifications include 10 Mb\100 Mb CAT 5 certified cable plant, Novell 3.1 or 4.1x, Windows/NT 3.51 or 4.0. The computer 200 is linked via LAN line 22 to at least one case manager workstation 23 (486-DX100, 16 Mb RAM, 50 Mb free on hard drive, Windows 3.1 or higher, SVGA display 800×600). This typically occurs by placing the exception record into a "review" database, which is monitored by a case manager at the host site. The case manager has access to the demographic database 201, the provider database 202, and the plan rules 203.

Host Computer Functions

Host site 20 comprises a host computer 200 that houses a database 201 of demographic and coverage information for the host's insured participants. The host modem 21 is configured for communication with the provider modem 33. Typically the modems 21,33 are not in constant communication; rather, uploads and downloads are scheduled at predetermined intervals, such as after close of business. These uploads and downloads also can carry messages other than data transfer, such as e-mail messages, during the connect, thus obviating at least some of the need for telephone calls.

The host computer 200 further houses a database 202 of providers accepted for treating patients. From this database 202 the referrals discussed above (FIG. 1, step 824) can be made to a patient desiring treatment based upon data such as geographical location and provider area(s) of specialization.

The transfer of patient information is preferably selective and hence subject to a filtering out of data not desired to be sent. For example, prior clinical data may be withheld for reasons of patient confidentiality.

The host computer 200 also houses the set of rules 203 associated with each patient's insurance plan as discussed above, which permits the host computer 200 to approve a treatment plan automatically for a particular patient and also permits the host computer 20 to approve a change in an already-approved treatment plan without seeking a case manager's approval.

In order to amass a large amount of patient treatment statistics, means are also provided for communicating selected patient data to a data-collection center 90 for building a national or regional database. Preferably patient information is filtered prior to transmission, such as by encrypting the patient's social security number, for ensuring patient confidentiality. Such a database would ultimately become sufficiently large that statistically valid conclusions could be drawn as to efficacy of various types of treatments, including patterns of interventions and medications. It is envisioned that such statistics could then be utilized to alter the rules governing preapproved treatment plans.

Treatment Plans

The treatment plan individualizes and defines the instruments and processes for the course of treatment, such as tests and questionnaires, extent and type of therapy, and level of care to be administered. Additionally, it serves as an electronic filter by which all activity in the patient chart is verified as an approved component of the plan. Therefore, as discussed above, all entries into the patient chart that are in accordance with the plan are preapproved when data are uploaded to the host computer 200.

Treatments plans may be general or specific in nature, depending upon the type of disorder being treated and the treatment approach. Treatment plans may be constructed item by item by the provider, or the provider may modify one of an existing set of treatment plan models. Treatment plans may also be downloaded from the host 20.

Provider Computer Functions

Provider computer 32 houses a database 321 of patient information. Upon opening the system, which has security features such as a requirement for entry of an ID and password, a patient list screen 51 (FIG. 3) appears. The list 514 that appears may be filtered by selecting among provider 511, patient status 512, and level of care 513, all of which have drop-down lists associated with them. This list 514 may also be sorted by name, social security number, chart ID number, or social security number of the insured, by selecting the desired item within the list sequence box 515. From this window 51 the user may add a new patient record 516, view a highlighted patient's record 517, or delete a patient record 518. In addition, a search can be performed by entering record information into the search box 519.

Once a desired patient's name 520 has been highlighted, that patient's electronic chart may be viewed either by double-clicking on the name 520, or by clicking on "View" 517, both of which provide entry into the Patient Master module 322.

From the patient list screen 51 the user may also navigate via icons 521 or menu bar items 522 to other sectors of the system. For example, the Scheduling 323 and Billing 325 modules are accessed via drop-down menus on the menu bar 522.

An additional feature of the patient list screen is an icon 510 providing a link to a diagnosis table that contains diagnostic labels and criteria set by the American Psychiatric Association in the DSM for all five axes. Hyperlinked text allows the provider to move rapidly from topic to topic and to review differential diagnosis. From the DSM reference screen a complete glossary of terms is also accessible.

The patient master screen 52 (FIG. 4) is the first point of entry into a selected patient's electronic chart and includes a template having plurality of data insertion locations, such as "Last Name" 523, including some with what are referred to in WindowsTM terms as a "combination list box" or "combo box," which contain data housed in a user-defined table. These boxes, such as "Marital Status" 524, are for entering demographic information. This type of screen and data entry thereinto are well known in the art.

From the patient master screen 52 the user may access other areas of the patient's electronic chart via a plurality of icons positioned across the top of the screen 52. These icons include, but are not intended to be limited to, "Patient Account" 525, "Session Master" 526, "Behavioral Outcomes Measurement System" 527, "Clinician's Summary of Change" 528, "Medications" 529, "Tests" 530, "History" 531, "Treatment Plan" 532, "Clinical Information" 533, "Addresses" 534, "Relationships" 535, "Referrals" 536, "Groups" 537, "Employment Information" 538, and "Insurance Information" 539. Each of these icons provides access to another screen from which desired information may be obtained. For example, clicking on the "Medications" icon 529 brings up the screen 54 shown in FIG. 5, which lists on the left-hand side the medications 541 prescribed for the patient and, on the right-hand side, dosage data 542. Medications may also be added 543 or deleted 544 by clicking on the appropriate screen location.

A record of all sessions is maintained within the provider computer 32. By clicking on the "Session Master" icon 526, the Session Master module 324 is entered, and the corresponding screen 55 appears (FIG. 6), which represents the patient's clinical, financial, and administrative information related to a treatment session. This module 324 is linked to the Schedule 323 and Billing 325 modules, so that, when an appointment is scheduled, a corresponding session entry record is created automatically. Session entry records can also be created manually.

On the Session Master screen 55 the user may view a scrollable list 551 of all patient appointments. As a selected appointment is highlighted 552, the corresponding session information appears on the right-hand side, including the Questionnaires administered 553, the Session Provider 554, and the CPT/Diagnosis 555 entered by the provider for that session.

Double-clicking on an appointment 552 causes the Session Maintenance screen 56 to open (FIG. 7), which may be reviewed, edited, or entered for recording data for a new session. Within the Appointment box 560 are located the Provider 561, Facility 562, Date and Time of Appointment 563, and CPT Billing Codes with Primary Diagnosis 564. If any of this information is desired to be changed, the edit icon 565 may be clicked, which causes the Appointment window 57 to open.

The Appointment window 57 (FIG. 8) includes a session box 571 containing the same information regarding Provider, Facility, Date and Time of appointment as the Session Maintenance window 56. Additional information is found in the CPT codes 572 and Diagnoses 573 boxes; should additional information be desired to be entered in these boxes, the Add from CPT Table 573 or Add from Diagnoses Table 574 buttons can be clicked, which launch windows containing a selection table, respectively, the Procedure Code Table or the Select Diagnosis table. The system will issue a warning if either the CPT code or the diagnosis is not approved on the patient's treatment plan. The CPT codes 572 must be linked to a Diagnosis 573 with the use of the left-pointing arrow 575, which copies the selected diagnosis under the CPT code. Without this link being made, the session cannot be posted for billing. This link is also important when it is desired to print of claim form, such as an HCFA 1500, which is used to submit claim on paper, under conditions in which billing is not performed electronically.

The treatment plan for a patient may be viewed or a new plan created by clicking on the appropriate icon 532 on the Patient Master window 52 (FIG. 4), which brings up the Treatment Plan window 58, shown containing an exemplary treatment plan box 581 in FIG. 9. When a plan is first created, by clicking on the Add button 588, a new case window appears, into which should be entered case information and additional demographic information and comments as desired. A provider can be assigned to the case by selecting one from a provider list.

A summary of managed care sessions appears on the lower right of the treatment plan window 58, with a Case Sessions box 582 and a Total Sessions box 585 containing numbers of Approved 583,586 and Used 584,587 Sessions, respectively.

Figure 10:
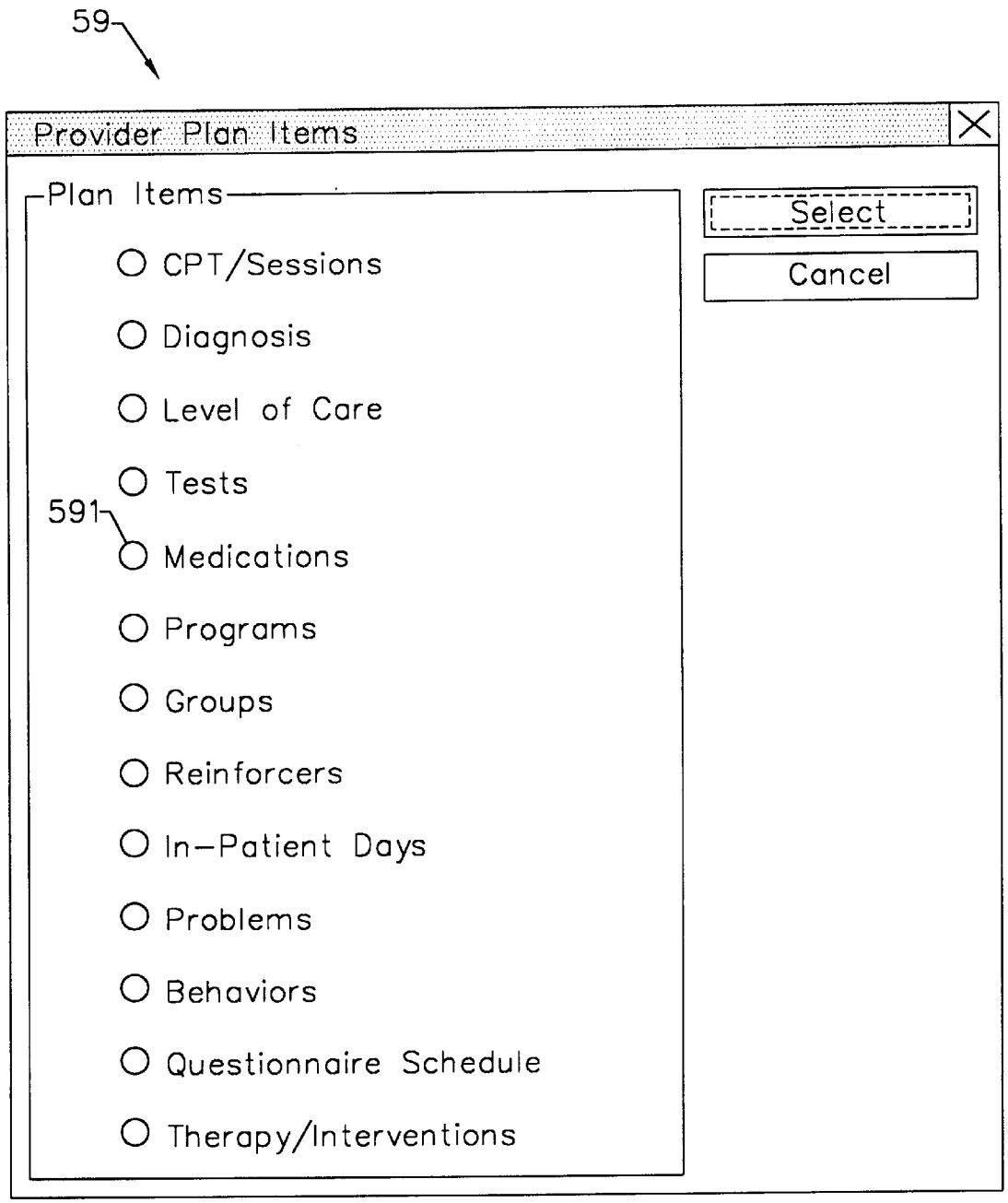
FIG. 10 illustrates an exemplary provider plan item screen.

In order to assign a plan element to the treatment plan, the Add button 588 is clicked on the Treatment Plan window, which brings up a list of Provider Plan Items 59 that have been approved for the chosen provider, an exemplary list being illustrated in FIG. 10. Clicking on one of these items brings up the associated screen; for example, selecting the "Medications" option 591 brings up the associated window 54 (FIG. 5).

Upon completion of a session, a billing may be initiated by returning to the Patient List window 51 (FIG. 3) and using a drop-down menu under the menu bar item "Billing" 510, from which the user may navigate to a patient accounts window, from which may be brought up for viewing such information as the patient's account ledger, insurance information, and outstanding charges. Clinical charges are automatically generated by the system upon linking a CPT code to a diagnosis and also by scheduling a new appointment. These charges can then be posted, either individually or in batch mode, by selecting the appropriate buttons within the billing module. Upon posting, the charges are uploaded when desired to the host site 20 for processing, where they are checked for automatic approval or referred to a case manager if necessary.

This upload of patient information to the host site 20 is preferably filtered as desired by the provider 30 to include only those data to which the host is entitled, for example, the results of questionnaires and/or tests specifically requested by the host treatment plan. Other data, such as session notes in narrative form, may be withheld if deemed appropriate by the provider. Alternatively, the selection of data to be sent can be defined by the system. As an example, the system may be designed to filter out such information as: provider personal (spouse information), questionnaires and tests administered that do not belong to the host and the clinician's personal notes.

Patient Treatment

Figure 11:
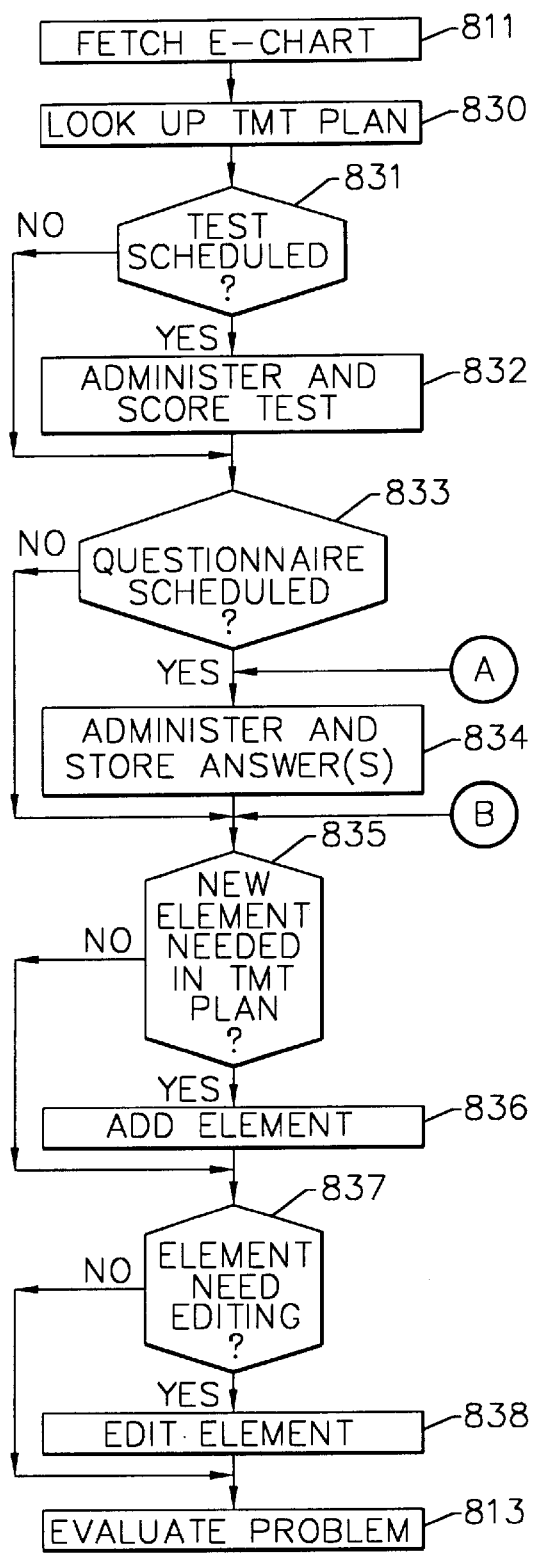
FIG. 11 is a flowchart of an exemplary treatment course.
Figure 12:
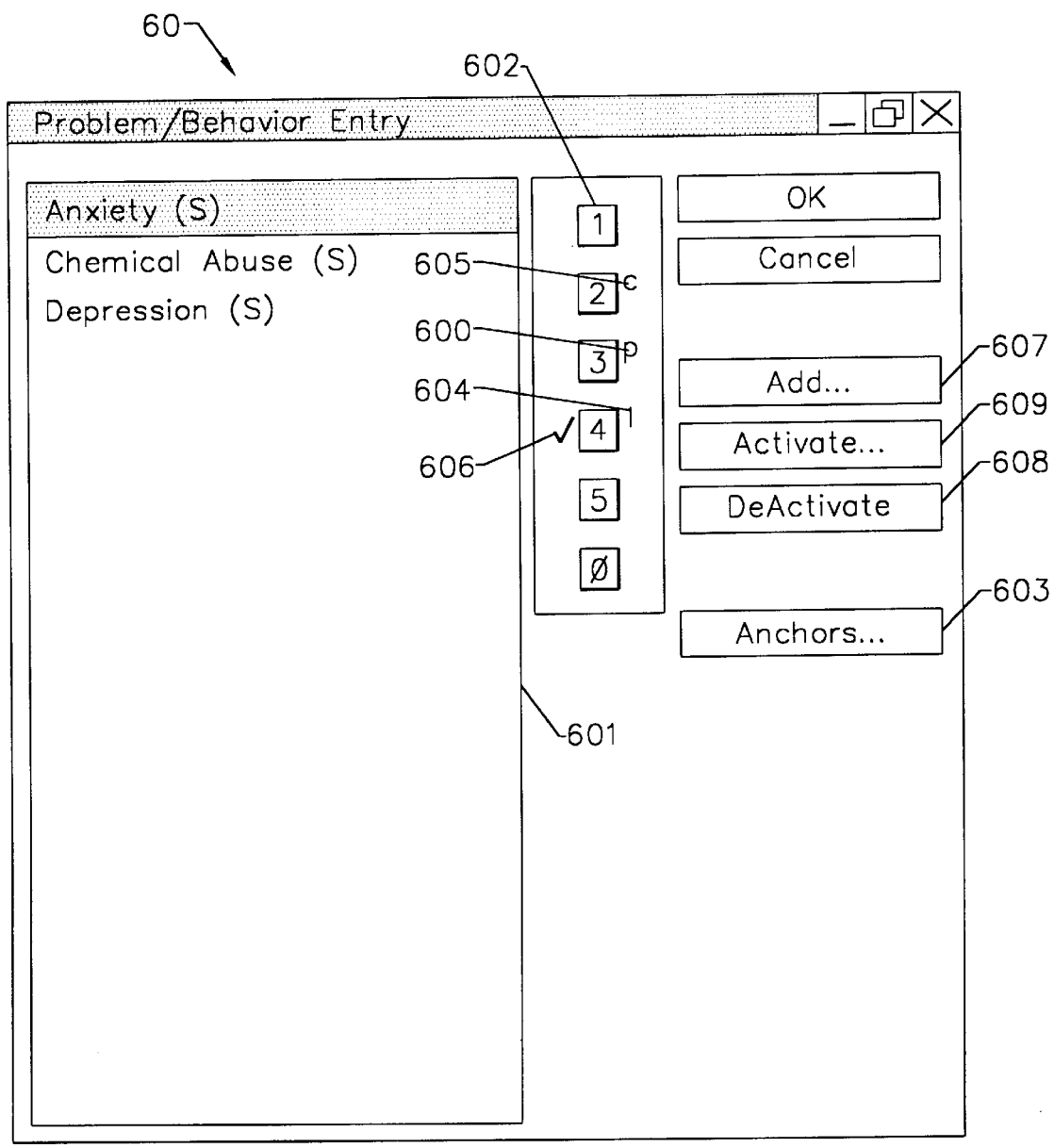
FIG. 12 illustrates an exemplary problem/behavior entry screen.
Figure 13:
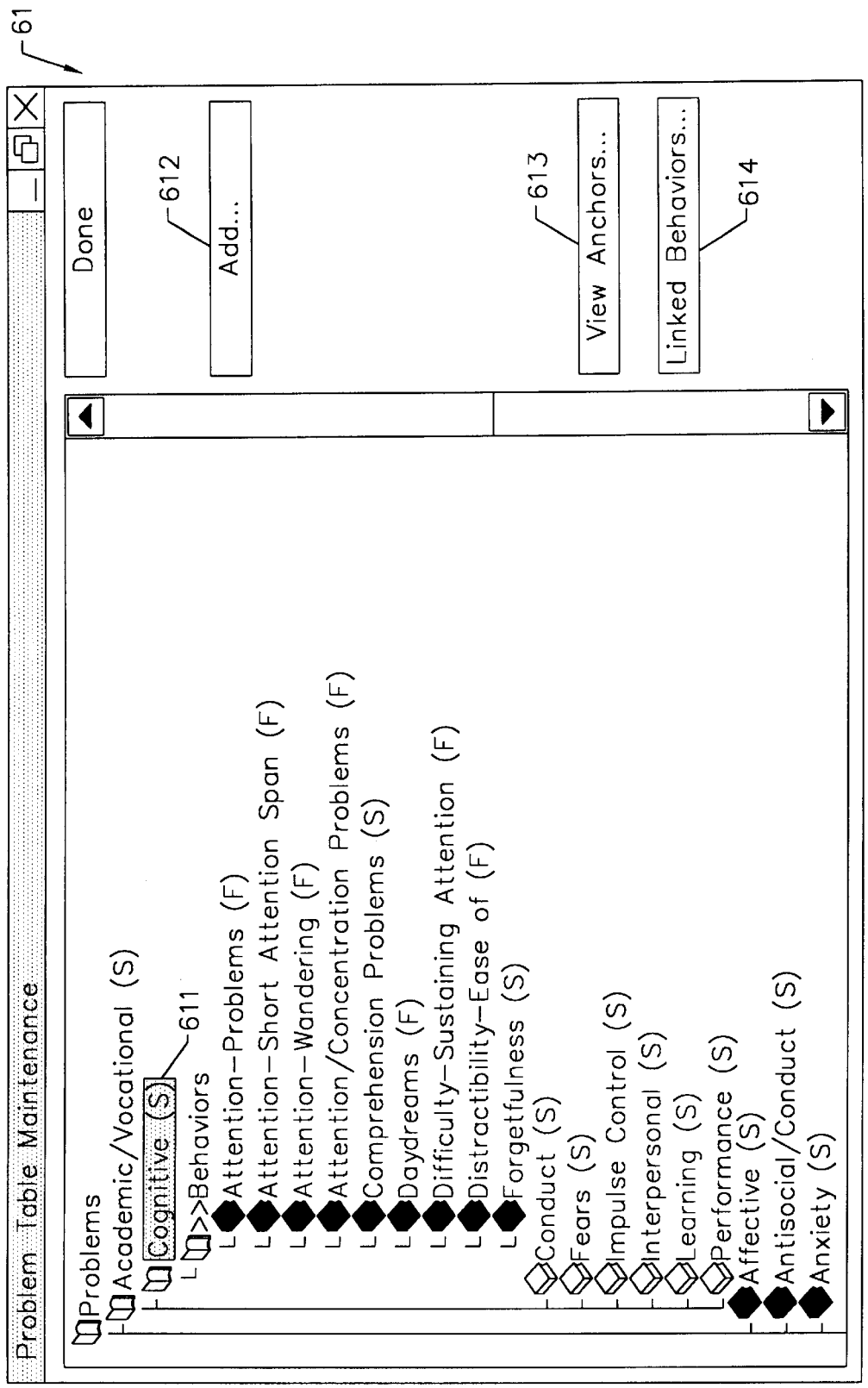
FIG. 13 illustrates an exemplary problem/behavior table screen.
Figure 14:
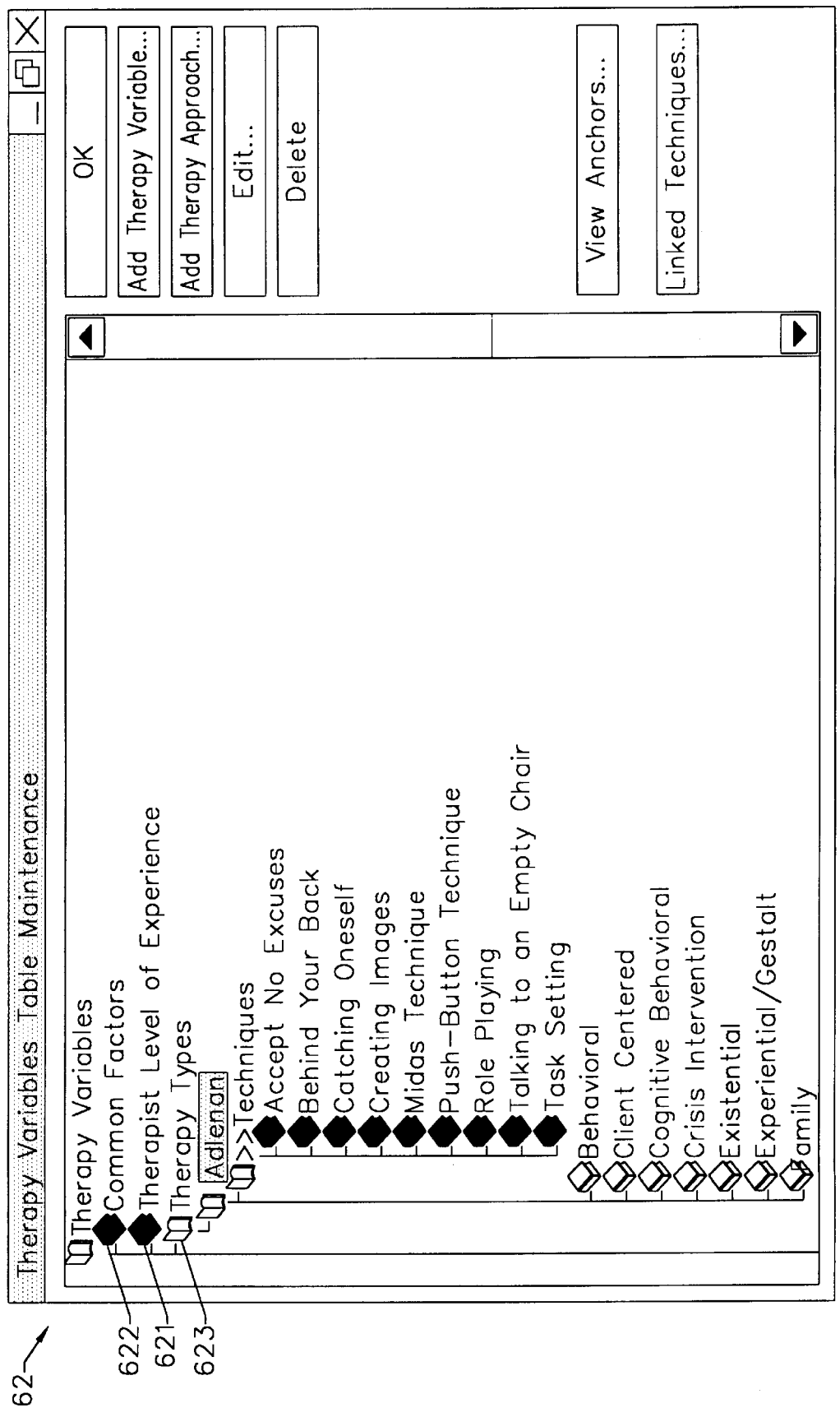
FIG. 14 illustrates an exemplary therapy variables table screen.
Figure 15:
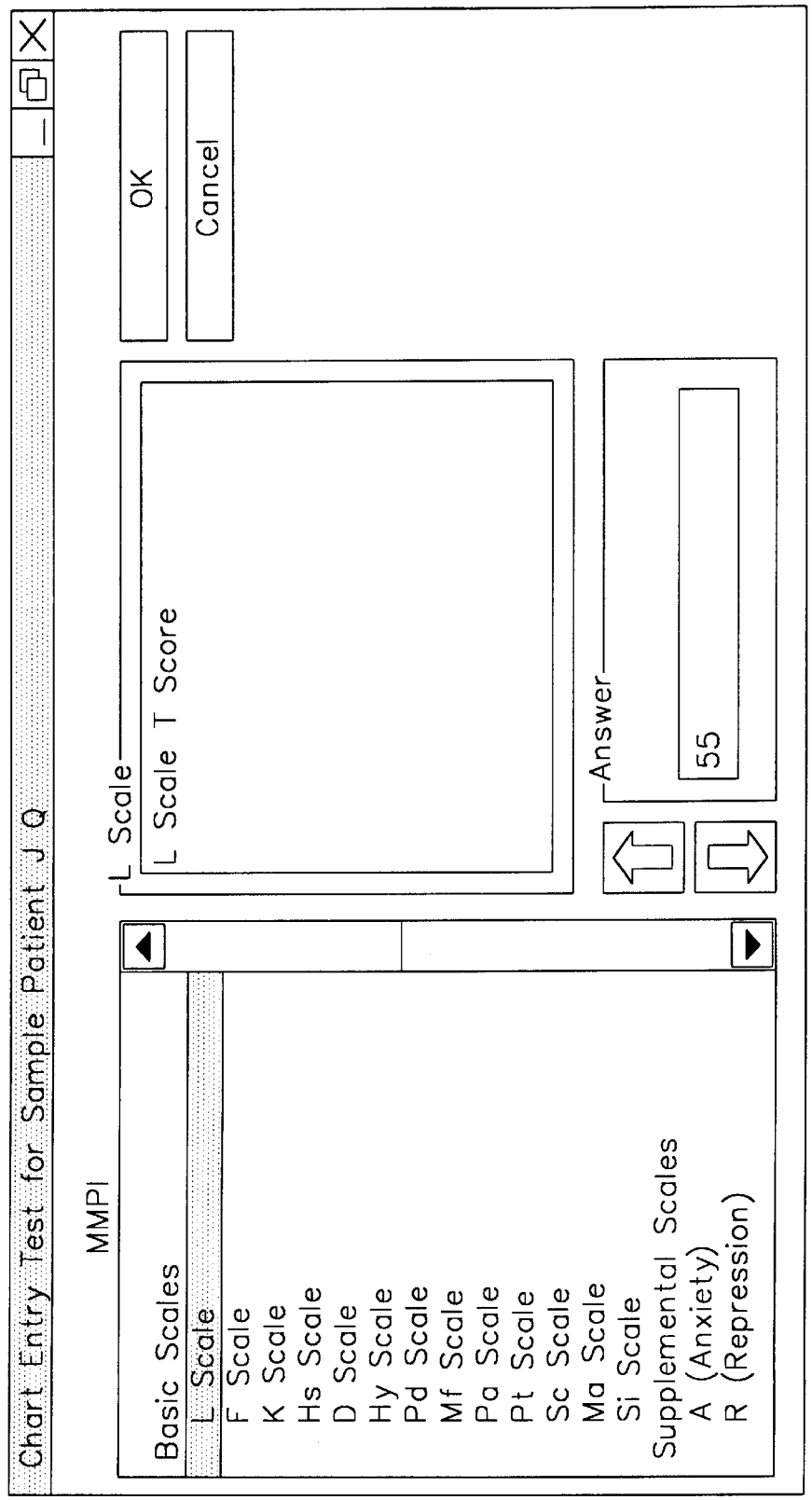
FIG. 15 illustrates an exemplary test screen.

Once the patient demographic data and treatment plan are resident in the provider computer 32, treatment can be initiated. A flowchart of an exemplary course of treatment is illustrated in FIG. 11, which expands upon step 812 of FIG. 1.

In step 811, the therapist looks up the patient's electronic chart, from which the treatment plan is looked up in step 830. The treatment plan (FIGS. 9 and 10) may include such features as a diagnosis, recommended medication, and a determination of level of care (e.g., outpatient), problem(s), behavior(s), therapy variables, tests, and questionnaires.

If a test is scheduled (step 831), it should be administered and scored (step 832); if a questionnaire is scheduled (step 833), it should be administered and the answers stored (step 834).

The therapist should also determine if a new element is needed in the treatment plan (step 835), and add it if needed (step 836); if an element should be edited (step 837), this should be performed (step 838). Finally, the problem(s) should be evaluated at step 813.

It should be noted that, if a new element is deemed by the therapist to be needed, approval may need to be sought from the host. This occurs as indicated in FIG. 1, beginning at step 808.

From the Session Maintenance screen 56 (FIG. 7) the provider can access and edit any of a set of linked screens related to the treatment plan:

The Medication screen 54 can be brought up by clicking the Enter button 567 in the Medication box 566. Here the provider can review dosage, quantity, refill, start dates, expiration dates, route of administration, reason for prescribing, and reason for discontinuing a medication. Scrolling through the medications list 541 causes the information in the respective fields to correspond to the medication selected.

The Problem/Behavior Entry screen 60 (FIG. 12) is brought up by clicking the Enter button 578 in the Problems/Therapy box 576. Each item in the list 601 has associated with it a behavioral anchor 602 that facilitates precision in rating. The anchor can be accessed by clicking the Anchor button 603. Upon intake, the therapist gives the patient an initial rating "I" 604 and a goal rating "G" 605. In subsequent sessions the therapist records the most current rating "✓" 606, and the previous rating "P" 600 is also displayed.

Behaviors/problems can be added to the treatment plan by clicking the Add button 607, which brings up a Problem/Behavior Table 61 (FIG. 13), can be deactivated 608 if goal attainment has been achieved, or can be reactivated 609 if problems/behaviors reemerge.

The Problem/Behavior Table 61 (FIG. 13) is used to add and rate items for the Problem/Behavior Entry screen 60. Once a particular behavior 611 is selected from the list 615, the Add button 612 is clicked. The letter "F" next to a behavior name indicates that it is measured by frequency; the letter "S," by severity. The anchors are viewed for the selected behavior by clicking the View Anchors button 613; likewise for the Linked Behaviors button 614. The problems list 615 comprises a tree-structured table, wherein subentries are displayed upon selecting a higher-level head.

The Therapy Information screen 62 (FIG. 14) is brought up by clicking the Enter button 577 in the Problems/Therapy box 576 of the Session Maintenance screen 56. Four types of information are available for describing or rating the therapy process: case complexity (not shown), which may be rated on a 1–5 Likert scale; therapist level of experience with various issues or interventions used in the session 621, also rated on a 1–5 Likert scale; common factors in psychotherapy 622, comprising 22 events that can take place in various types of psychotherapy, selected ones of which ratable as to their relative contribution to the effectiveness of a given session; and therapy types 623, wherein the relative significance of various generic interventions or specific techniques associated with various schools of thought are rated to assess the relative contribution of the effectiveness of a given session.

As shown in FIG. 11 at step 832, the patient's treatment plan may comprise an administration of one or more tests, perhaps readministered at a preselected interval. The Test screen 63 (FIG. 15) is brought up by clicking the Enter button 569 in the Test/Questionnaire box 568 of the Session Maintenance screen 56, and displays patient scores for tests recorded in a view-only format. Typically the test will have been administered separately, such as on paper, scored, and the results entered by clicking the Edit button.

The patient's treatment plan additionally may comprise an administration of one or more questionnaires, which here are defined as an instrument comprising items selected from a database of questions. The system of the present invention permits virtually unlimited flexibility in using, modifying, and creating such questionnaires. One feature is the ability to transmit questionnaires between the host and the provider; for example, a host may download a questionnaire for administration to a particular patient, in which case that questionnaire will become a part of the provider's database. The host may further designate that questionnaire as copyright protected, in which case that questionnaire would not be approved for use for patients not covered by that host. Likewise, a provider can create and indicate as copyright protected its own questionnaire(s) and prevent their being uploaded to a host site.

Figure 16:
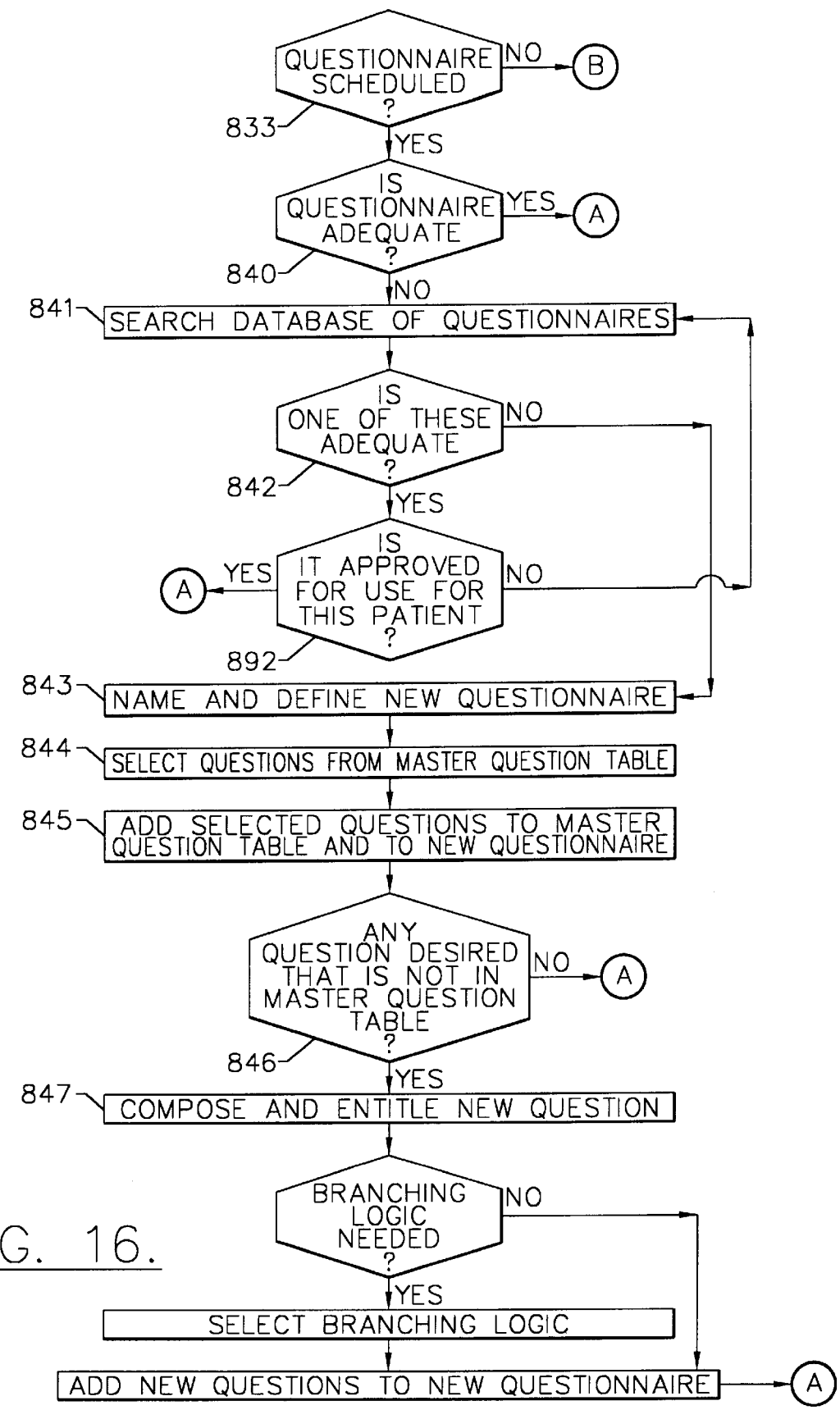
FIG. 16 is a flowchart for choosing and creating a new questionnaire.

A flowchart of the process of choosing and creating a questionnaire is given in FIG. 16.

Figure 17:
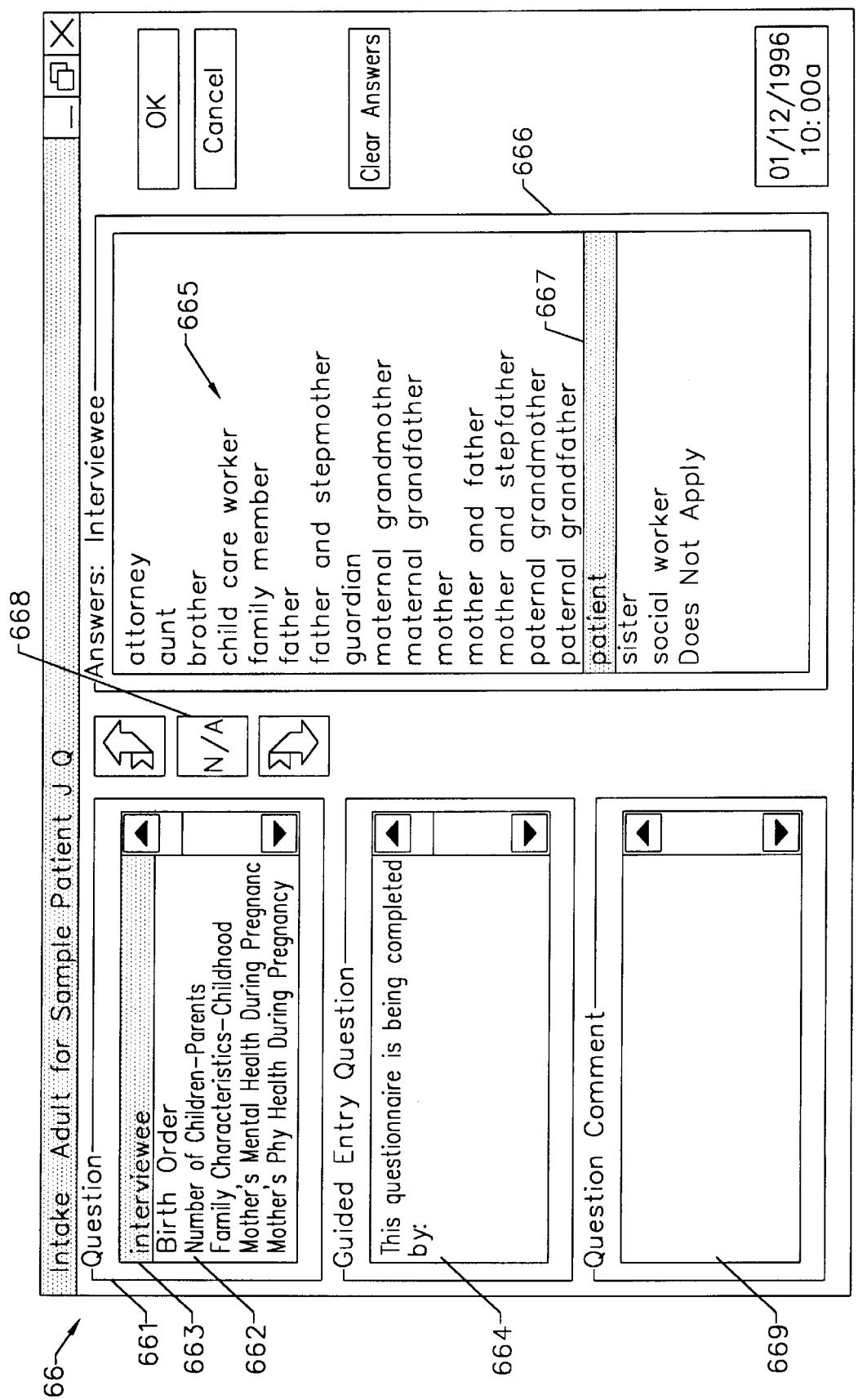
FIG. 17 illustrates an exemplary questionnaire screen, here an adult intake questionnaire.
Figure 19:
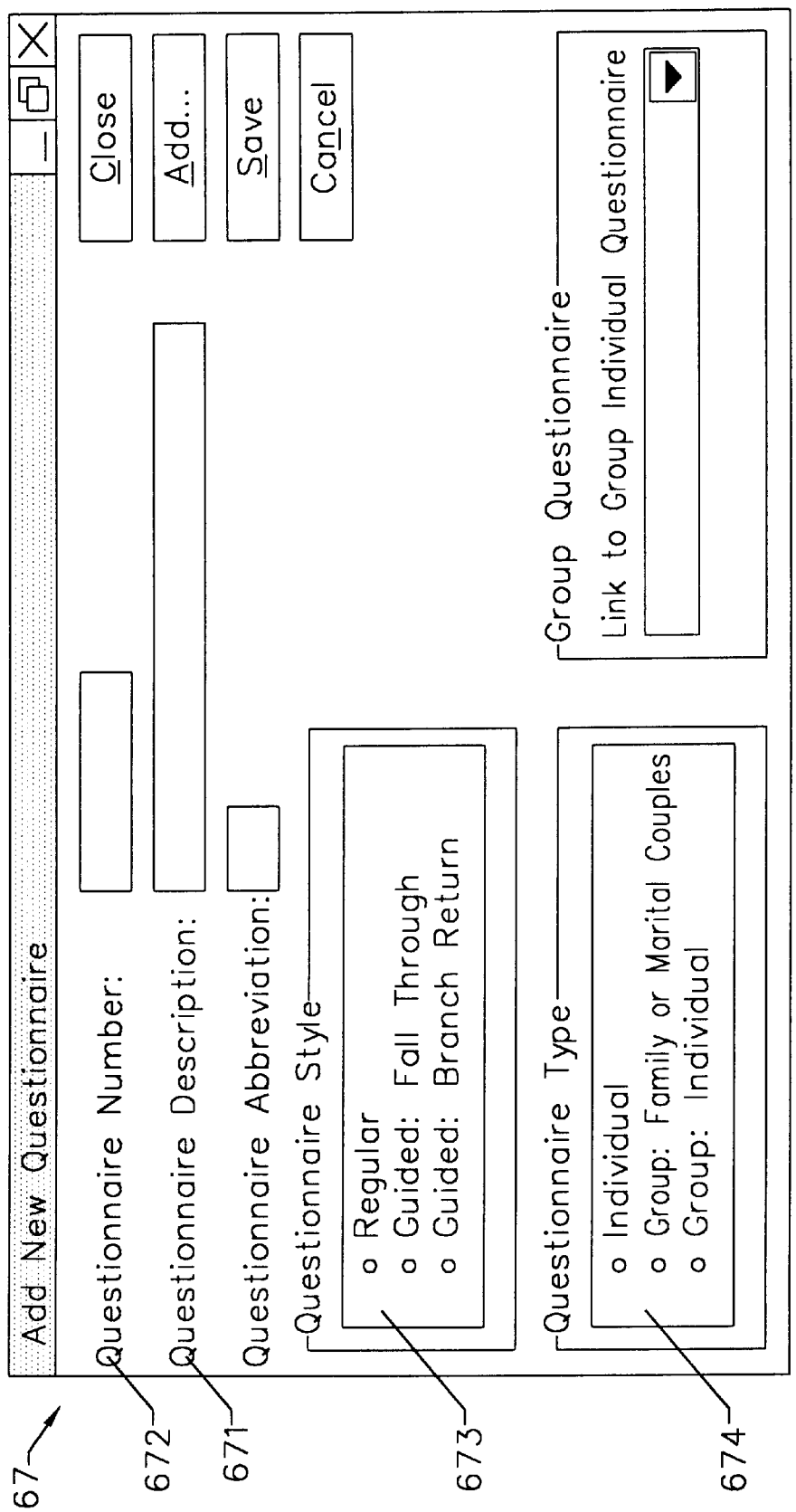
FIG. 19 illustrates an exemplary add new questionnaire screen.

If a questionnaire is scheduled, which is indicated by the "yes" answer to decision step 833 of FIG. 11, and if the therapist determines that the scheduled questionnaire is adequate at step 840, it is administered as indicated at step 834 in FIG. 11. An example of a questionnaire screen in the database is shown in FIG. 17, an adult intake questionnaire.

The questionnaire template 66 comprises a Question box 661 containing a scrollable list 662 of question topics. When a topic is highlighted 663, the associated narrative question is displayed in the Guided Entry Question box 664. A list of answers 665 is provided in the Answer box 666, and the correct answer 667 is highlighted and clicked to enter it as a response. The answer list 665 may comprise descriptive or informational items, some of which may permit more than one answer, or a Likert rating, allowing only one response. The N/A button 668 defaults to the answer Does Not Apply. Notepad-type narrative comments may also be entered in the Question Comment box 669.

If, however, the scheduled questionnaire is not deemed adequate, the therapist will typically want to administer a different one, and will search the select questionnaire screen at step 841 (FIG. 16). If one among these is deemed adequate at step 842, then it should be checked if that questionnaire is usable for that patient at step 892. If it is, that one is brought up and administered as at step 834 of FIG. 11. If it is not, for example, if the questionnaire is "owned" by a different host from that covering the present patient, the questionnaire database will need to be searched again at step 841 until a usable and acceptable questionnaire is located.

Another feature of the system is that it provides a warning if the selected questionnaire is not part of the approved treatment plan. In this case, approval should be sought from the host site for its administration.

It may happen, however, that none of those among the database of questionnaires is considered adequate, in which case a new questionnaire can be constructed with the tools of the present invention. A new questionnaire may be created entirely de novo, or edited from a cloned version of an existing questionnaire that approximates that which the therapist desires. The therapist brings up the Add New Questionnaire screen 67 (FIG. 19), gives it a name 671, number 672, style 673, and type 674 at step 843. Then questions are selected at step 844 from the master question table (FIG. 20), which contains all the questions resident at that time in the database. The master question table 64 may comprise questions initially resident in the system, questions mandated by the host, and/or questions created by the provider. Each "question" within the master question table 64 contains all the possible answers that may be selected during session entry.

Each item 642 in the master question table 64 falls within one of six functional categories 641, comprising: single-answer questions, Likert-scaleable questions, multiple-answer questions, comment-only questions, calculation questions, and headers. Single-answer questions may include those requiring a yes/no answer, or a quantification of a characteristic, such as "ability to make work decisions." Multiple-answer questions allow for more than one answer, such as symptoms experienced. Comment-only questions permit narrative text to be entered. Calculation questions display the results of calculations such as test score summaries. Headers are used to indicate a new area of questioning that will appear in a narrative note, to be discussed in the following.

A question is chosen from the master question table 64 using the Select Questions screen 68 (FIG. 21), from which the questions 681 are chosen and added at step 845 to the new questionnaire. If the questionnaire is now acceptable (step 846), it can be administered as at step 834 in FIG. 11.

Another feature of the system of the present invention is that the user can also program in a custom guided-entry pattern, wherein the answer to a question determines whether the next question in sequence is asked. For example, if the patient has no history of alcohol abuse, the alcohol-related questions will be skipped.

It may also happen that questions are desired to be entered into the new questionnaire that are not a part of the master question table, determined at step 846. In this case new questions are composed at step 847 with the use of the Add New Question screen 69 (FIG. 22), by naming the question 691, forming the verbiage of the question 692, indicating whether it is Likert scaleable 693, what the entry option is 694, and what the question type is 695.

The questionnaire should now be in a form desired, and it can be administered as at step 834 in FIG. 11.

Reporting of Behavioral Health Care Outcomes

Individual Patient Reporting

The system of the present invention permits great flexibility in extracting and presenting data sorted and aggregated as directed by the user, whether the provider or host. Reports can be prepared directed to any one particular patient or with the use of cross-tabulations to collect data from a plurality of patients.

Figure 23:
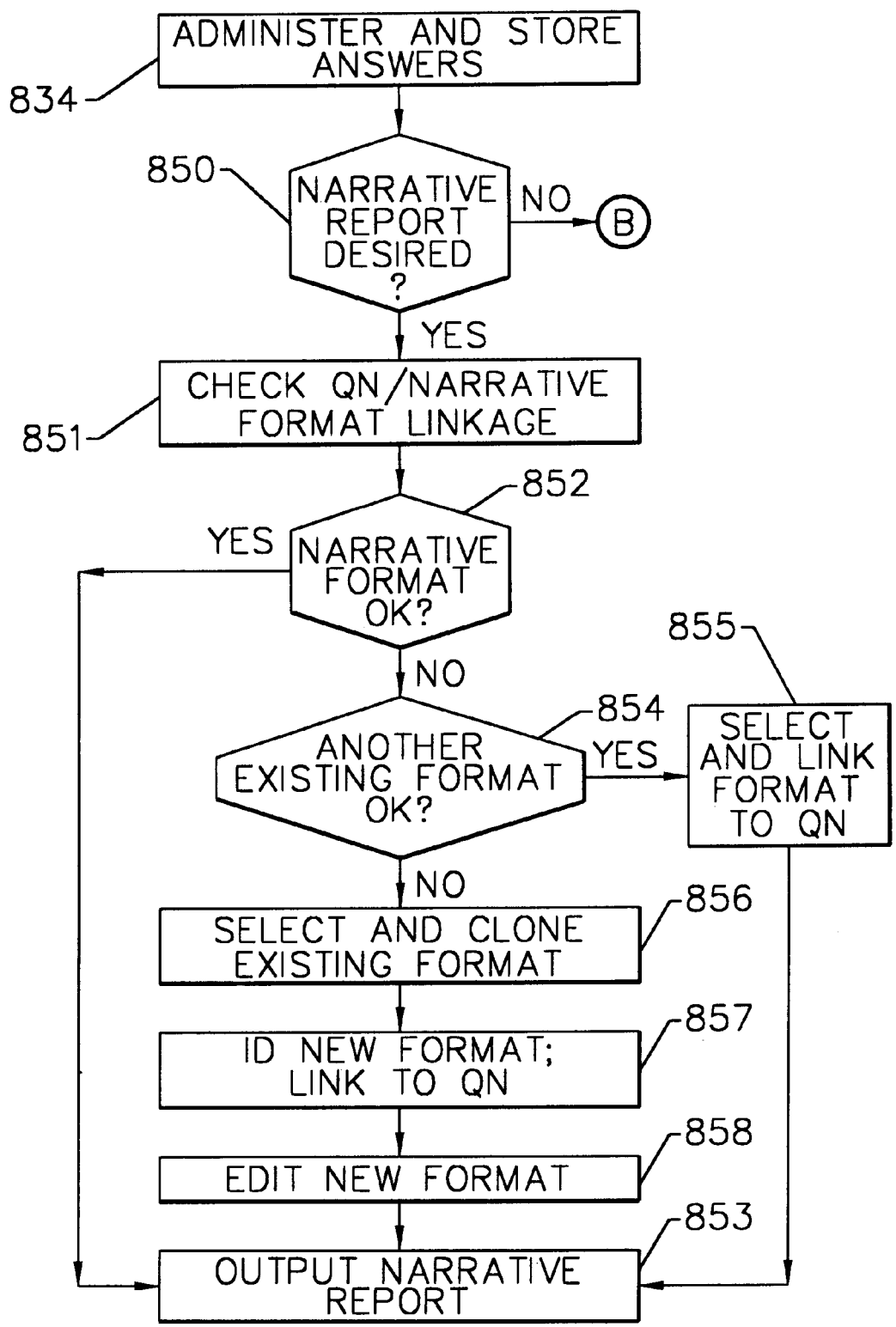
FIG. 23 is a flowchart for the creation of a narrative report.

One of the reporting vehicles resident within the system comprises a means for forming and outputting a narrative report from a patient's data already entered into the system, as shown in the flowchart of FIG. 23. This figure proceeds from the step 834 of administering a questionnaire and storing the answers in FIG. 11, if a narrative report is desired (step 850).

A narrative note format serves as the framework for outputting a narrative note. Each format is linked to a particular questionnaire (QN), although a questionnaire can be administered without choosing or creating a narrative note format. The linkage can be checked by accessing the questionnaire/narrative linkage screen 78 (step 851, FIG. 23A), which is a read-only list. If the linked narrative note format is acceptable as is (step 852), the narrative report can be output, for example, to a printer or to a file, or it can be previewed on the screen (step 853).

If the linked format is not acceptable, another existing format can be looked up (step 854) on the narrative notes format screen 70 (FIG. 24), which lists format IDs 701 and descriptions 702. A format is selected (step 855) by linking the questionnaire to that format, and a report is output (step 853) under the direction of the format elements. Alternatively, a format that is close can be selected, cloned, and edited, or a new one can be created de novo. Preferably the therapist selects and clones an existing format (step 856) such as the "New Clinical Report Format," which is set up as a template and is resident in the system and on which can be built a new narrative format. The new format is identified with a new name, description, and link to a questionnaire at step 857 and edited in the Edit Narrative Format screen 71 (FIG. 25) at step 858.

Each format contains a series of discrete sentences that have words in angle brackets indicative of a datum that will be inserted from the patient's electronic chart when the report is output. For example, in the editing box 711 of FIG. 25, <@Name (Last)-Patient@> would fetch the patient's last name from the chart and insert it at that point in the narrative.

Figure 25:
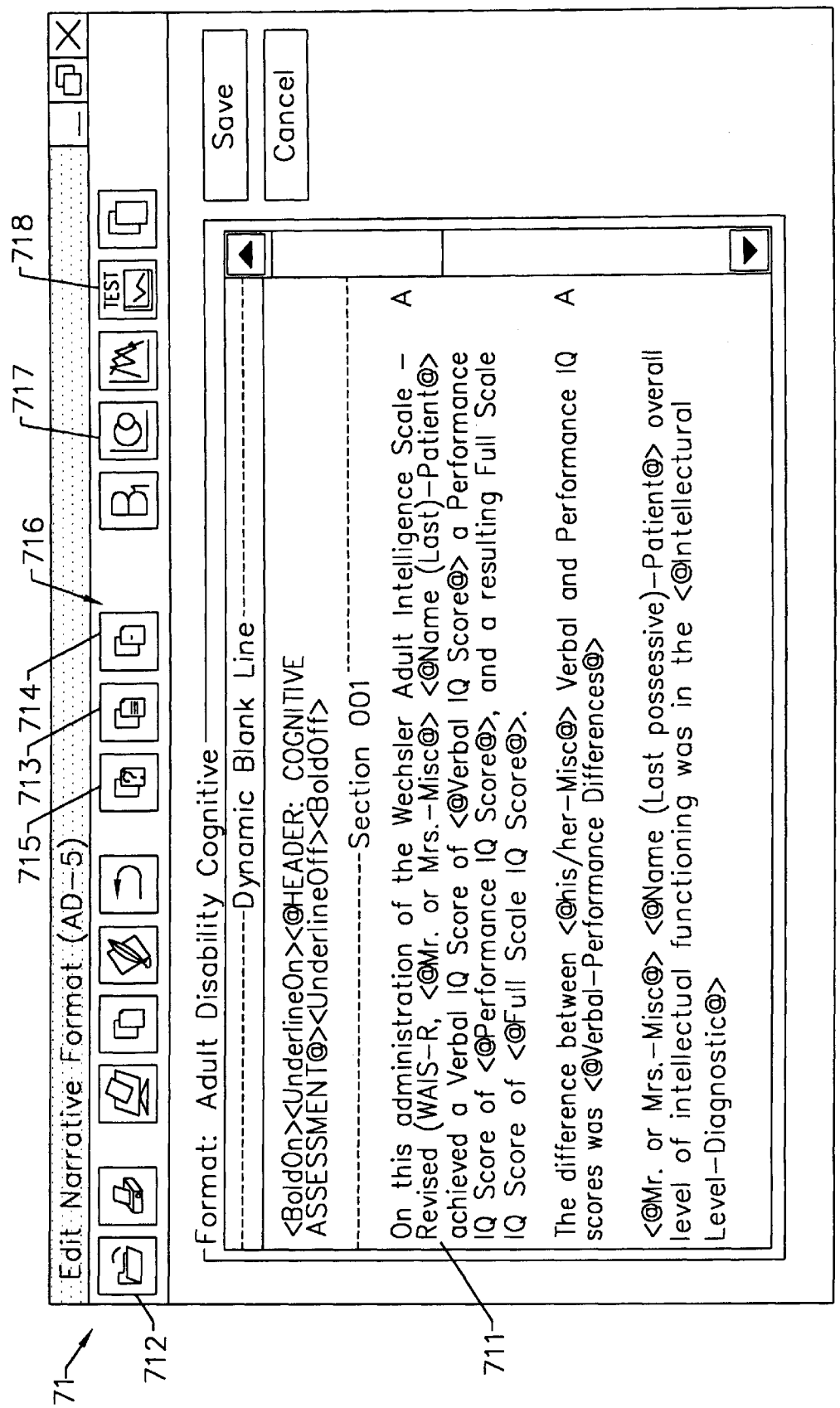
FIG. 25 illustrates an exemplary screen for editing the narrative note format.

Editing the displayed format is accomplished by clicking on the appropriate icon from the tool bar menu 712 in FIG. 25. For example, selecting the "insert sentence" icon 713 permits the user to insert a title or new sentence into the format; similarly for the "insert word" icon 714. A narrative form of a question can also be inserted by selecting the "insert question" icon 715, which brings up a screen containing all the questions resident in the system and from which the answers thereto can also be accessed to ensure that they make sense in the context of the narrative.

Additionally, behaviors can be inserted by selecting the appropriate icon 716 that have been targeted for treatment for the patient. A summary is added into the narrative, including ratings such as goal and current session, goal and rating the last five sessions, or a description only.

The answers for selected questions can be used to create calculation fields within a questionnaire. Calculations can be performed within a narrative format utilizing Likert scales by selecting the "insert formula" icon 717, which brings up a window permitting the user to create an arithmetic formula for aggregating question results, the result of which calculation is inserted into the narrative format at the chosen location. Similarly, test results can be inserted by selecting the "tests" icon 718.

An example of a narrative format and the resulting narrative report for a particular patient is shown in FIGS. 26A,B and 27A,B, respectively. It should be noted that the report need not be output at each administration of the questionnaire, but it can be output whenever desired.

An indication of how the system creates a report is provided by comparing the narrative note format shown in FIGS. 26A,B with the corresponding output report shown in FIGS. 27A,B. For example, item 261 reads: <@Mr. or Mrs.-Misc.@> <@Name (Last possessive)-Patient@> attitude was <@Attitude-Client@>. To create this sentence the system thus must retrieve three data items from the patient's electronic chart, and yields the report sentence 271: Dr. Sample-Patient's attitude was overly solicitous, provocative and resistive.

Another important feature of the present invention is a behavioral outcomes measurement (BOM) system, which comprises a means for graphically tracking problem and behavior Likert ratings and questionnaire Likert ratings for a particular patient. In addition, the medications and types of interventions can be superimposed upon the graphs, permitting great flexibility in outcomes presentation.

Figure 28:
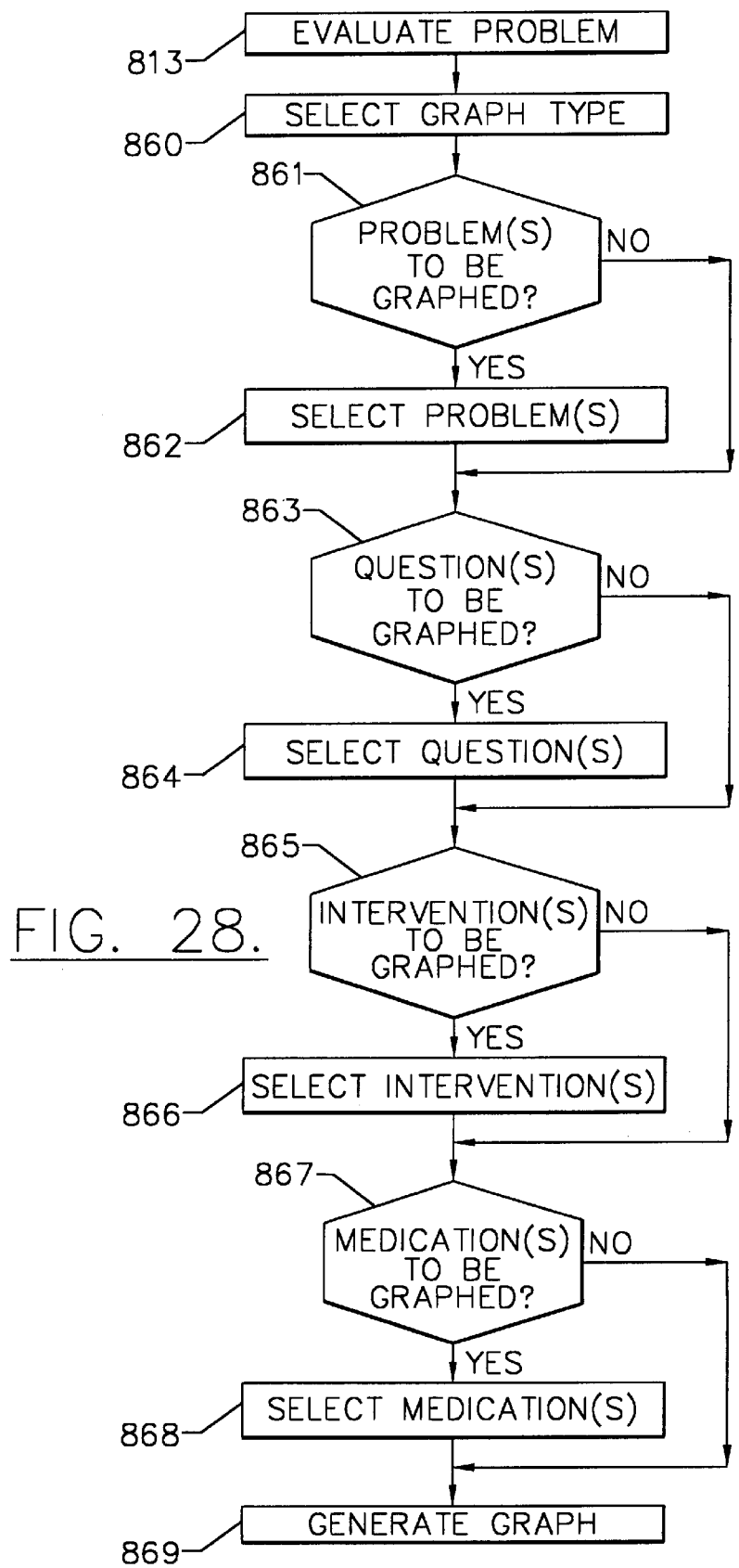
FIG. 28 is a flowchart for behavioral outcomes measurement.

A flowchart of the BOM system is presented in FIG. 28. Typically such a graph will be desired following a plurality of treatment sessions, such as after a problem evaluation at step 813 of FIG. 1.

Figure 29:
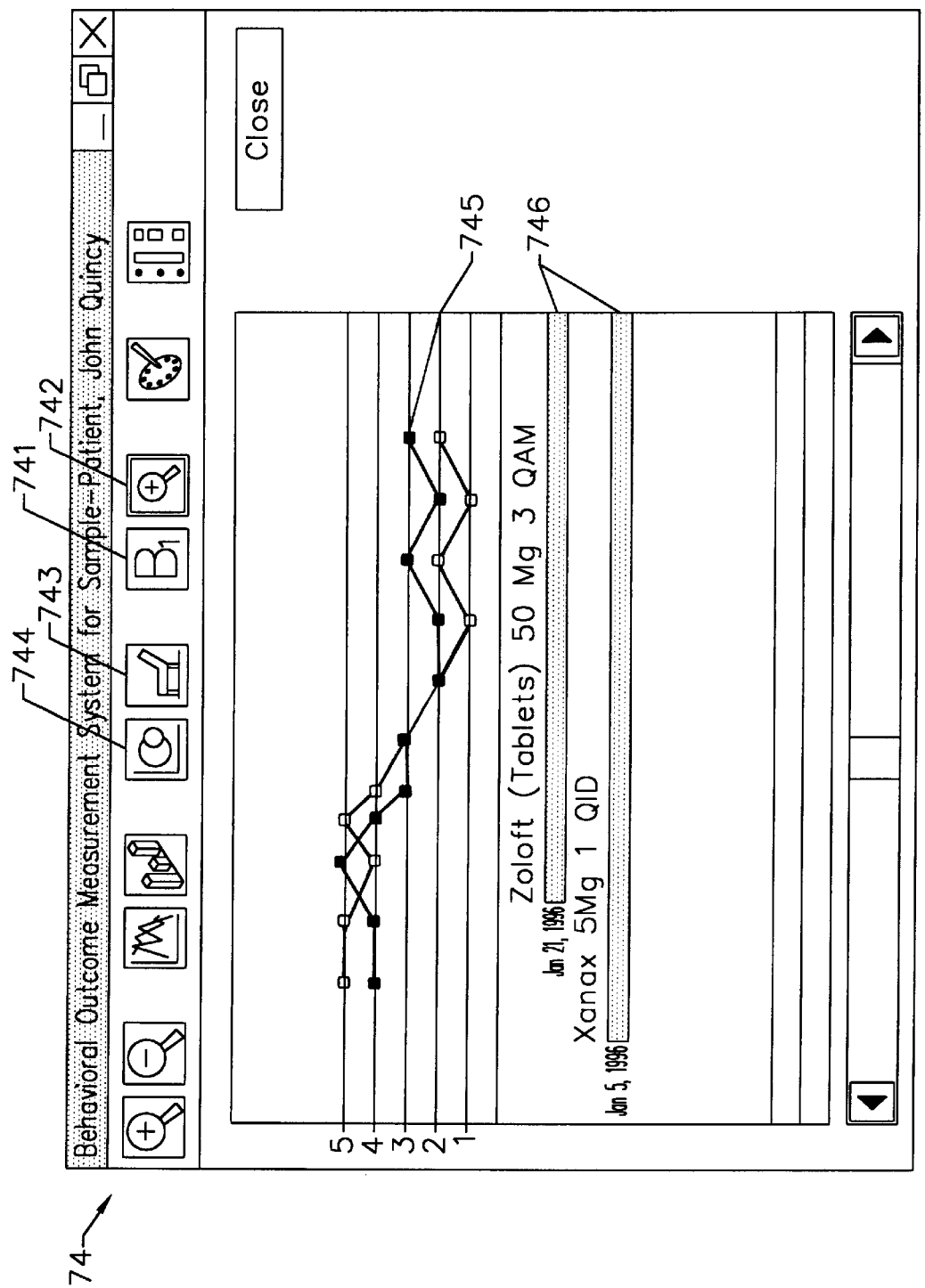
FIG. 29 is an exemplary line graph generated by the behavioral outcomes measurement system.
Figure 30:
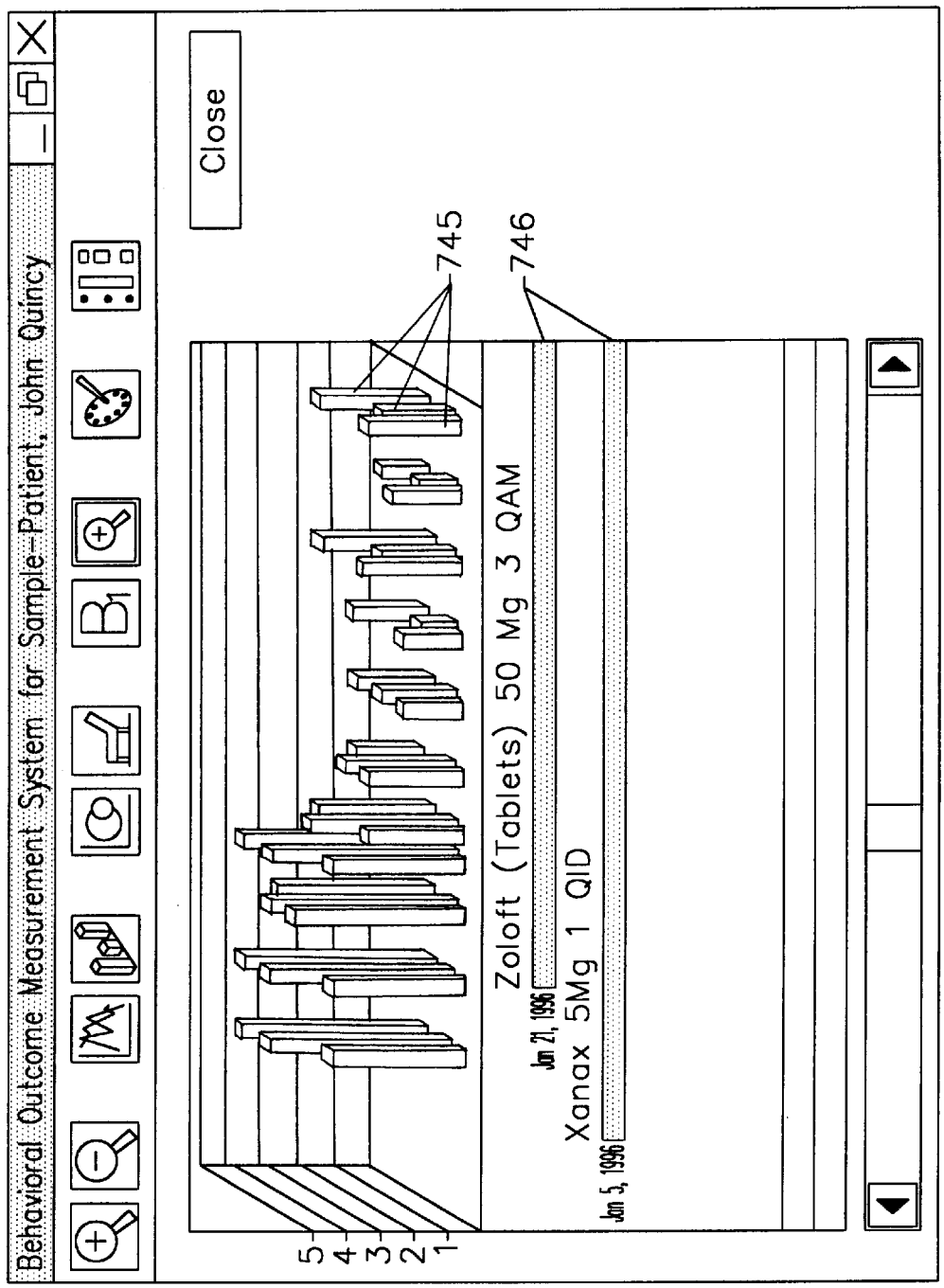
FIG. 30 is an exemplary bar graph generated by the behavioral outcomes measurement system.

There are two types of graph that can be made with a preferred embodiment of the system of the present invention, although these types are not intended to be limiting: a line graph 74, such as illustrated in FIG. 29, or a bar graph 75, such as illustrated in FIG. 30. Which graph type is desired is chosen at step 860. Other options are also available, such as color and the time span and dates to be visualized.

The therapist can make decisions for graph elements by selecting the appropriate icon from the tool bar menu on FIGS. 29 and 30. Those referred to herein are shown in FIG. 29. The therapist can decide whether to graph problems and behaviors at step 861; if so, one or more is selected at step 862 for presentation (icon 741). A decision whether to graph Likert-scaled questionnaire items is made at step 863; those desired are selected at step 864 (icon 742). A decision whether to graph interventions and/or therapies is made at step 865; those desired are selected at step 866 (icon 743). Finally, a decision whether to graph medications is made at step 867; those desired are selected at step 868 (icon 744). The graph is generated at step 869.

It should be noted that these decision steps need not occur in the order presented in FIG. 28. In FIGS. 29 and 30 are the line graph and bar graph for an exemplary case illustrating three items (745) being graphed on a Likert (1–5) scale with time and a simultaneous presentation of two medications (746) tracking the time during which they were being prescribed.

Followup Questionnaires and Data Extraction

Additional features of the system of the present invention comprise means for extracting and aggregating data for a plurality of patients, typically sorted by one or more criteria, for the purposes of accumulating patient statistics and thereby enabling treatment to be optimized.

The system comprises means for creating a followup questionnaire group, for performing such functions as assessing treatment, patient satisfaction, and referral source tracking, although these are not intended to be limiting. This system module can be used to create lists of patients, providers, and/or referrals who will receive a followup questionnaire, typically on hard copy via mailing. Such questionnaires can be constructed at the host or the provider site, although those issuing from the provider site will likely encompass only those patients within its database.

Figure 31:
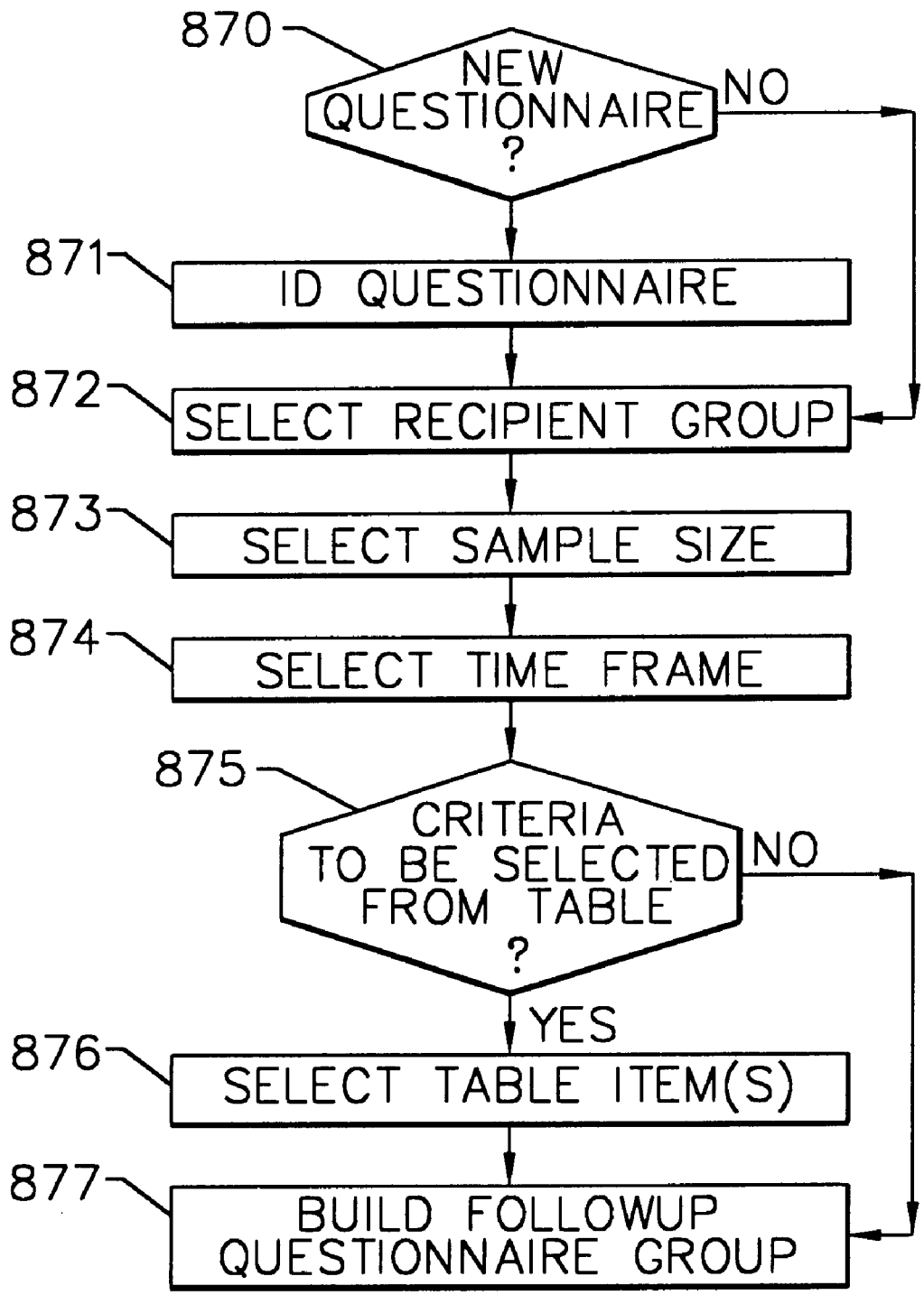
FIG. 31 is a flowchart for creating a recipient group for sending a followup questionnaire.

A new followup questionnaire group is created as illustrated in the flowchart of FIG. 31 with the use of screen 76 (FIG. 32) and the accessing of the appropriate databases described previously. First it is decided at step 870 whether an already-created questionnaire is to be used. If not, the followup questionnaire is provided with a title 761 at step 871. A recipient group 762 is chosen at step 872, which may include, for example, patients, providers of record, providers of session, or referrals. A sample size 763 is chosen at step 873, which may be "all" or some maximum number, in which case the system will randomly select a group of individuals who meed the group size chosen. Finally, a time frame 764 is chosen at step 874 during which the treatment occurred.

A choice can be made at step 875 to impose additional filters, which occurs at step 876. Sorting can be accomplished by the system on the basis of any of the tables in the database, including the master question table, questionnaires, problems, and behaviors. For example, the user can choose to select all patients receiving zoloft who have been treated for depression at a particular clinic.

Once all the choices have been made, the followup questionnaire group can be built at step 877 and mailing labels printed.

Figure 33:
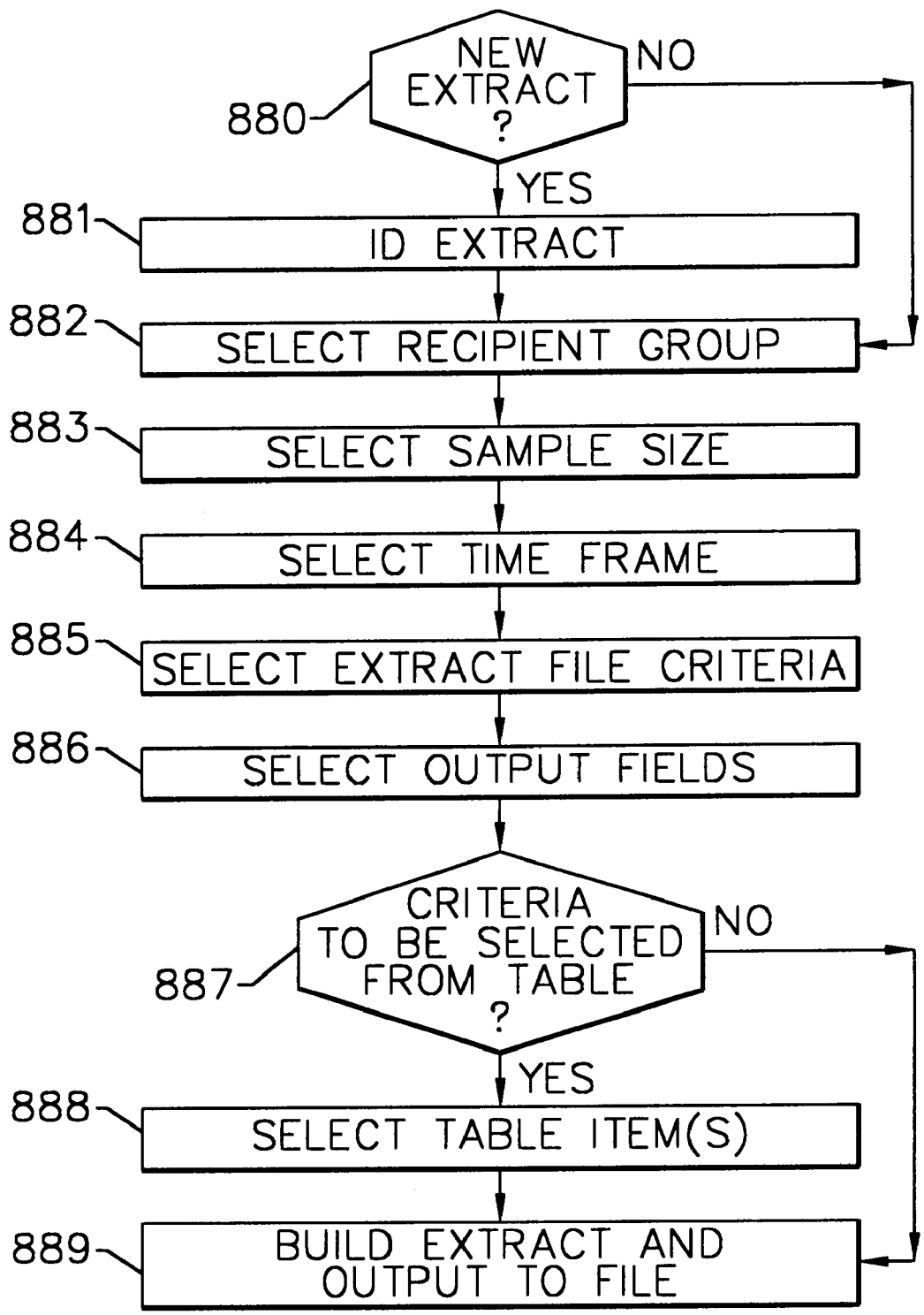
FIG. 33 is a flowchart for creating a data extract from the database.

In similar fashion, data extraction can be accomplished as illustrated in the flowchart of FIG. 33, generating files derived from queries of the databases. Thus the user can generate data extracts containing the results of searches based on user-defined specifications. The files created with this module can be imported into a spreadsheet, database, or statistical package for generating graphs and reports. As with the followup questionnaire group construction, criteria such as demographic data and clinical factors can be used to select a group of individuals for the query.

First it is decided at step 880 whether an already-created extract formula is to be used. If not, the new extract report is provided with a title at step 881. A recipient group is chosen at step 882, which may include, for example, patients, providers of record, providers of session, or referrals. A sample size is chosen at step 883, which may be "all" or some maximum number, in which case the system will randomly select a group of individuals who meed the group size chosen. Finally, a time frame is chosen at step 884 during which the treatment occurred.

Figure 34:
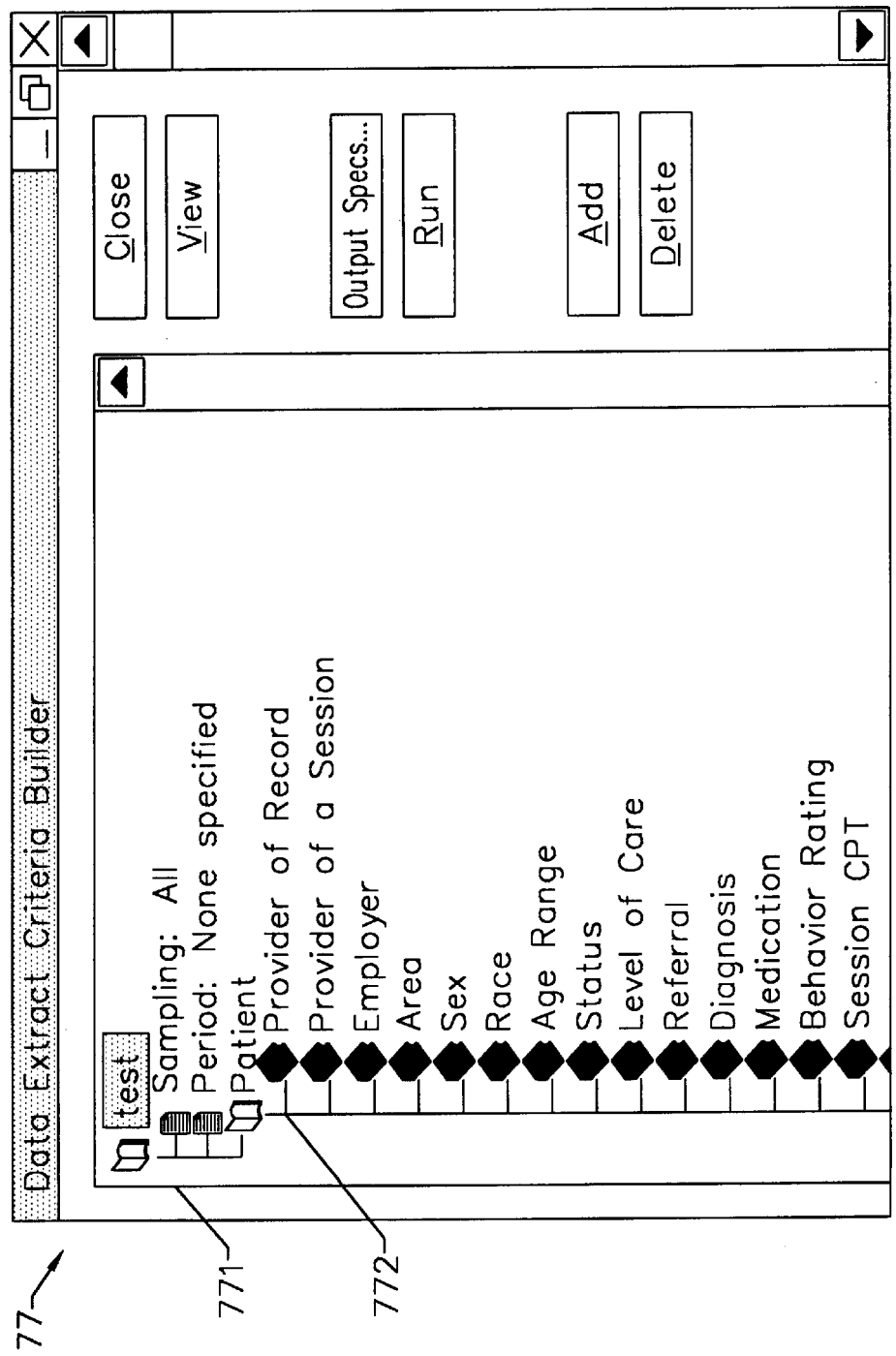
FIG. 34 illustrates an exemplary screen for building the criteria for performing the data extract.

Next the extract file criteria are chosen at step 885 from a screen 77 illustrated in FIG. 34. This embodiment of the table comprises a tree-browser window 771, from which criteria 772 are chosen that will form the basis for creating the extract file list (e.g., age range, patient sex, employees, etc.). This procedure builds the patient list from which specific data will be extracted.

When an item has been selected, a list of output selections are provided, from which a category of information may be chosen at step 886. For example, if "patient medication" was chosen at step 885, the user may select "Prozac™." Steps 885 and 886 may be repeated as needed to add filter criteria.

A choice can be made at step 887 to impose additional filters, which occurs at step 888. Sorting can be accomplished, as for the followup questionnaire, by the system on the basis of any of the tables in the database, including the master question table, questionnaires, problems, and behaviors. Once all the choices have been made, the extract data can be built at step 889 and output to a designated file.

It may be appreciated by one skilled in the art that additional embodiments may be contemplated that are not necessarily limited to the behavioral health care arena, including an analogous system and method for any medical or occupational/physical therapy information system.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. A method for reporting behavioral health care and status of a patient comprising the steps of:
   providing a database comprising at least one patient electronic chart including:
      patient demographic information;
      an answer to a behavioral health assessment question administered to the patient;
   providing a database including at least one narrative note format, the narrative note format comprising:
      fixed text material; and
      link indicators interspersed within the text material having means for pointing to specific data in the chart database, at least one link indicator related to patient demographic information and at least one link indicator related to the assessment answer;
   selecting a narrative note format from the database;
   integrating the narrative note format with the patient chart data pointed to by the link indicators; and
   outputting a report comprising a narrative-style text including information specific to the patient from the patient chart.

2. The method recited in claim 1, wherein:

the answer comprises a numerically scaled answer;

the integrating step further comprises translating the numerically scaled answer into text, for forming a narrative report having the linked assessment answer in verbal form.

3. The method recited in claim 2, wherein the translating step comprises correlating the numerically scaled answer to an anchor.

4. The method recited in claim 2, wherein:

the answer comprises a plurality of numerically scaled answers;

the narrative note format further includes a calculation indicator having a plurality of link indicators to, and a formula for, directing an arithmetic operation on at least two numerically scaled answers; and the integrating step further comprises utilizing the formula to perform the arithmetic operation on the indicated numerically scaled answers for including a result therefrom in the report.

5. A method for creating a custom report on the behavioral health care and status of a patient comprising the steps of:

providing a database resident in a computer, the database comprising at least one patient electronic chart including:

patient demographic information;

an answer to a behavioral health assessment question administered to the patient;

composing a narrative note format comprising:

fixed text material; and link indicators interspersed within the text material having means for pointing to specific data in the chart database, at least one link indicator related to patient demographic information and at least one link indicator related to the assessment answer;

storing the narrative note format in the computer;

integrating the narrative note format with the patient chart data pointed to by the link indicators; and outputting a report comprising the integrated narrative-style text including information specific to the patient from the patient chart.

6. The method recited in claim 5, the answer comprises a numerically scaled answer;

the integrating step further comprises translating the numerically scaled answer into text, for forming a narrative report having the linked assessment answer in verbal form.

7. The method recited in claim 6, wherein the translating step comprises correlating the numerically scaled answer to an anchor.

8. The method recited in claim 5, wherein:

the answer comprises a plurality of numerically scaled answers;

the narrative note format further includes a calculation indicator having a plurality of link indicators to, and a formula for, directing an arithmetic operation on at least two numerically scaled answers; and the integrating step further comprises utilizing the formula to perform the arithmetic operation on the indicated numerically scaled answers for including a result therefrom in the report.

9. A system for reporting behavioral health care and status of a patient comprising:

a computer having resident therein a database comprising:

at least one patient electronic chart including:

patient demographic information;

an answer to a behavioral health assessment question administered to the patient;

at least one narrative note format, the narrative note format comprising:

fixed text material; and link indicators interspersed within the text material having means for pointing to specific data in the chart database, at least one link indicator related to patient demographic information and at least one link indicator related to the assessment answer;

input means for displaying a list of narrative note formats in the database and for selecting a narrative note format therefrom;

software means for integrating the narrative note format with the patient chart data pointed to by the link indicators; and means for outputting a report comprising a narrative-style text including information specific to the patient from the patient chart.

10. The system recited in claim 9, wherein:

the answer comprises a plurality of numerically scaled answers;

the narrative note format further includes a calculation indicator having a plurality of link indicators to, and a formula for, directing an arithmetic operation on at least two numerically scaled answers; and the integrating means further comprises means for utilizing the formula to perform the arithmetic operation on the indicated numerically scaled answers for including a result therefrom in the report.

11. A system for creating a custom report on the behavioral health care and status of a patient comprising:

a computer having resident therein a database comprising at least one patient electronic chart including:

patient demographic information;

an answer to a behavioral health assessment question administered to the patient;

input means for composing and entering a narrative note format into the computer comprising:

fixed text material; and link indicators interspersed within the text material having means for pointing to specific data in the chart database, at least one link indicator related to patient demographic information and at least one link indicator related to the assessment answer;

software means resident in the computer for integrating the narrative note format with the patient chart data pointed to by the link indicators; and means for outputting a report from the computer comprising the integrated narrative-style text including information specific to the patient from the patient chart.

12. The system recited in claim 11, wherein:

the answer comprises a plurality of numerically scaled answers;

the narrative note format further includes a calculation indicator having a plurality of link indicators to, and a formula for, directing an arithmetic operation on at least two numerically scaled answers; and the integrating means further comprises means for utilizing the formula to perform the arithmetic operation on the indicated numerically scaled answers for including a result therefrom in the report.

* * * * *